(12) United States Patent
Hogan et al.

(10) Patent No.: US 12,365,898 B2
(45) Date of Patent: Jul. 22, 2025

(54) CALCIUM CHANNEL 3.2 INHIBITORY PEPTIDES AND USES THEREOF

(71) Applicant: The Medical College of Wisconsin, Inc., Milwaukee, WI (US)

(72) Inventors: Quinn H. Hogan, Milwaukee, WI (US); Hongwei Yu, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 0 days.

(21) Appl. No.: 17/853,296

(22) Filed: Jun. 29, 2022

(65) Prior Publication Data

US 2023/0018405 A1    Jan. 19, 2023

Related U.S. Application Data

(60) Provisional application No. 63/216,032, filed on Jun. 29, 2021.

(51) Int. Cl.

| | | |
|---|---|---|
| *A61K 38/10* | (2006.01) | |
| *A61K 48/00* | (2006.01) | |
| *C07K 7/08* | (2006.01) | |
| *C07K 14/47* | (2006.01) | |
| *C12N 15/113* | (2010.01) | |
| *C12N 15/86* | (2006.01) | |
| *C12N 15/861* | (2006.01) | |

(52) U.S. Cl.
CPC .......... *C12N 15/113* (2013.01); *C12N 15/861* (2013.01); *C12N 2750/14142* (2013.01)

(58) Field of Classification Search
CPC ................ A61K 38/10; A61K 38/1709; A61K 38/1738; C07K 7/08; C07K 14/47; C07K 14/4728; C07K 14/4702; C07K 2319/60; C12N 15/113; C12N 15/86; C12N 15/861; C12N 2750/14142
See application file for complete search history.

(56) References Cited

U.S. PATENT DOCUMENTS

| | | |
|---|---|---|
| 2005/0074850 A1 | 4/2005 | Nadler et al. |
| 2006/0147946 A1 | 7/2006 | Akiva et al. |
| 2007/0178462 A1 | 8/2007 | Uebele et al. |
| 2007/0178553 A1 | 8/2007 | Snutch et al. |

FOREIGN PATENT DOCUMENTS

| | | |
|---|---|---|
| WO | 2014/045126 A2 | 3/2014 |
| WO | WO-2022217285 A1 * | 10/2022 |

OTHER PUBLICATIONS

U.S. Appl. No. 63/172,792, FD=Apr. 9, 2021 (Year: 2021).*
Wang, Guangfu et al., Genes & Development, 2015, 29:1535-1551.
Anderson, D. et al., Regulation of Neuronal Activity by Cav3-Kv4 Channel Signaling Complexes, Nature Neuroscience, 2010, 13(3):333-337.
Bezencon, O. et al., Discovery and Evaluation of Cav3.2-Selective T-Type Calcium Channel Blockers, Bioorganic & Medicinal Chemistry Letters, 2017, 27(23):5326-5331.
Buning, H. et al., Capsid Modifications for Targeting and Improving the Efficacy of AAV Vectors, Molecular Therapy Methods & Clinical Development, 2019, 12:248-265.
Cai, W. et al., MicroRNA-182 Alleviates Neuropathic Pain by Regulating Nav1.7 Following Spared Nerve Injury in Rats, Scientific Reports, 2018, 8(1):16750, pp. 1-11.
Cai, S. et al., Targeting T-type/CaV3.2 Channels for Chronic Pain, Translational Research, 2021, 234:20-30.
Catterall, W., Voltage-Gated Calcium Channels, Cold Spring Harbor Perspectives in Biology, 2011, 3:a003947, pp. 1-23.
Chan, K. et al., Engineered AAVs for Efficient Noninvasive Gene Delivery to the Central and Peripheral Nervous Systems, Nature Neuroscience, 2017, 20(8):1172-1179.
Chemin, J. et al., Calmodulin Regulates Cav3 T-type Channels at their Gating Brake, Journal of Biological Chemistry, 2017, 292(49):20010-20031.
Chen, W. et al., Accumulation of Cav3.2 T-type Calcium Channels in the Uninjured Sural Nerve Contributes to Neuropathic Pain in Rats with Spared Nerve Injury, Frontiers in Molecular Neuroscience, 2018, vol. 11, Article 24, pp. 1-13.
Choe, W et al., TTA-P2 is a Potent and Selective Blocker of T-type Calcium Channels in Rat Sensory Neurons and a Novel Antinociceptive Agent, Molecular Pharmacology, 2011, 80(5):900-910.
Deverman, B. et al., Cre-Dependent Selection Yields AAV Variants for Widespread Gene Transfer to the Adult Brain, Nature Biotechnology, 2016, 34(2):204-209.
Fan, J. et al., Down-Regulation of T-type Cav3.2 Channels by Hyperpolarization-activated Cyclic Nucleotide-gated Channel 1 (HCN1): Evidence of a Signaling Complex, Channels, 2017, 11(5):434-443.
Fischer, G. et al., Sustained Relief of Neuropathic Pain by AAV-Targeted Expression of CBD3 Peptide in Rat Dorsal Root Ganglion, Gene Therapy, 2014, 21(1):44-51.
Gadotti, V et al., Cav3. 2 T-Type Calcium Channels Control Acute Itch in Mice, Molecular Brain, 2020, 13:119, 7 pages.
Gao, G. et al., Clades of Adeno-Associated Viruses are Widely Disseminated in Human Tissues, Journal of Virology, 2004, 78(12):6381-6388.

(Continued)

*Primary Examiner* — Julie Ha
(74) *Attorney, Agent, or Firm* — Quarles & Brady LLP

(57) ABSTRACT

Aspects of the disclosure relate to constructs comprising one or more Cav3.2 inhibitory polypeptide that blocks Cav3.2 T-type calcium channel activity and nociceptive dorsal root ganglion (DRG) neuron excitation. Also provided herein are methods for treating pain in a subject in need thereof. In particular, provided herein are methods comprising administering Cav3.2 inhibitory peptide constructs to a dorsal root ganglion of the subject, whereby expression of the Cav3.2 inhibitory polypeptides partially or fully inhibits Cav3.2 T-type calcium channel activity in the DRG.

**21 Claims, 15 Drawing Sheets
(14 of 15 Drawing Sheet(s) Filed in Color)
Specification includes a Sequence Listing.**

(56) References Cited

OTHER PUBLICATIONS

Garcia-Caballero, A. et al., The Deubiquitinating Enzyme USP5 Modulates Neuropathic and Inflammatory Pain by Enhancing Cav3.2 Channel Activity, Neuron, 2014, 83:1144-1158.

Gomez, K. et al., Cdk5-Dependent Phosphorylation of CaV3.2 T-type Channels: Possible Role in Nerve Ligation-Induced Neuropathic Allodynia and the Compound Action Potential in Primary Afferent C Fibers, Journal of Neuroscience, 2020, 40(2):283-296.

Huang, C. et al., Physical Interaction Between Calcineurin and Cav3.2 T-type Ca2+ Channel Modulates their Functions, FEBS Letters, 2013, 587(12):1723-1730.

Huc, S. et al., Regulation of T-type Calcium Channels: Signalling Pathways and Functional Implications, Biochimica et Biophysica Acta, 2009, 1793(6):947-952.

Hudry, E. et al., Efficient Gene Transfer to the Central Nervous System by Single-Stranded Anc80L65, Molecular Therapy Methods & Clinical Development, 2018, 10:197-209.

Joksimovic, S. et al., Selective Inhibition of CaV3.2 Channels Reverses Hyperexcitability of Peripheral Nociceptors and Alleviates Postsurgical Pain, Science Signaling, 2018, 11(545):eaao4425, 29 pages.

Kerckhove, N. et al., Efficacy and Safety of a T-type Calcium Channel Blocker in Patients with Neuropathic Pain: A Proof-of-Concept, Randomized, Double-Blind and Controlled Trial, European Journal of Pain, 2018, 22(7): 1321-1330.

Liu, Q. et al., Upregulation of Cav3.2 T-type Calcium Channels in Adjacent Intact L4 Dorsal Root Ganglion Neurons in Neuropathic Pain Rats with L5 Spinal Nerve Ligation, Neuroscience Research, 2019, 142:30-37.

Monteil, A. et al., Inhibition of Cav3.2 T-type Calcium Channels by its Intracellular I-II Loop, Journal of Biological Chemistry, 2015, 290(26):16168-16176.

Nelson, M. et al., The Endogenous Redox Agent L-cysteine Induces T-type Ca2+ Channel-dependent Sensitization of a Novel Subpopulation of Rat Peripheral Nociceptors, Journal of Neuroscience, 2005, 25(38):8766-8775.

Perez-Reyes, E., G Protein-Mediated Inhibition of Cav3.2 T-type Channels Revisited, Molecular Pharmacology, 2010, 77(2):136-138.

Rehak, R. et al., Low Voltage Activation of KCa1.1 Current by Cav3-KCa1.1 Complexes, PLOS ONE, 2013, 8(4):e61844, pp. 1-16.

Reverdatto, S. et al., Peptide Aptamers: Development and Applications, Current Topics in Medicinal Chemistry, 2015, 15(12):1082-1101.

Rzhepetskyy, Y. et al., A Cav3.2/Stac1 Molecular Complex Controls T-type Channel Expression at the Plasma Membrane, Channels, 2016, 10(5):346-354.

Shin, S. et al., Enhanced T-Type Calcium Channel 3.2 Activity in Sensory Neurons Contributes to Neuropathic-Like Pain of Monosodium Iodoacetate-Induced Knee Osteoarthritis, Molecular Pain, 2020, 16:1-15.

Todorovic, S. et al., Regulation of T-Type Calcium Channels in the Peripheral Pain Pathway, Channels, 2007, 1 (4):238-245.

Todorovic, S. et al., Targeting of CaV3.2 T-Type Calcium Channels in Peripheral Sensory Neurons for the Treatment of Painful Diabetic Neuropathy, Pflüugers Archiv-European Journal of Physiology, 2014, 466:701-706.

Tomita, S. et al., Critical Role of Cav3.2 T-Type Calcium Channels in the Peripheral Neuropathy Induced by Bortezomib, a Proteasome-Inhibiting Chemotherapeutic Agent, in Mice, Toxicology, 2019, 413:33-39.

Wallace, M. et al., A Randomized, Double-Blind, Placebo-Controlled, Crossover Study of the T-type Calcium Channel Blocker ABT-639 in an Intradermal Capsaicin Experimental Pain Model in Healthy Adults, Pain Medicine, 2016, 17(3):551-560.

Wang, L. et al., Single Stranded Adeno-Associated Virus Achieves Efficient Gene Transfer to Anterior Segment in the Mouse Eye, PLoS One, 2017, 12(8):e0182473, pp. 1-12.

Watanabe, M. et al., Expression and Regulation of Cav3.2 T-Type Calcium Channels During Inflammatory Hyperalgesia in Mouse Dorsal Root Ganglion Neurons, PLOS ONE, 2015, 10(5):e0127572, pp. 1-19.

Weiss, N. et al., A Cav3.2/syntaxin-1A Signaling Complex Controls T-type Channel Activity and Low-threshold Exocytosis, Journal of Biological Chemistry, 2012, 287(4):2810-2818.

Whalley, K. et al., Blocking Painful Interactions, Nature Reviews Neuroscience, 2011, 12:431.

Yu, H. et al., AAV-Encoded CaV2.2 Peptide Aptamer CBD3A6K for Primary Sensory Neuron-Targeted Treatment of Established Neuropathic Pain, Gene Therapy, 2019, 26(7):308-323.

Ziegler, D. et al., A Randomized Double-Blind, Placebo-, and Active-Controlled Study of T-type Calcium Channel Blocker ABT-639 in Patients with Diabetic Peripheral Neuropathic Pain, Pain, 2015, 156(10):2013-2020.

PCT International Search Report and Written Opinion, PCT/US2022/035509, Sep. 28, 2022, 10 pages.

Extended European Search Report, dated Mar. 21, 2025, 8 pages.

\* cited by examiner

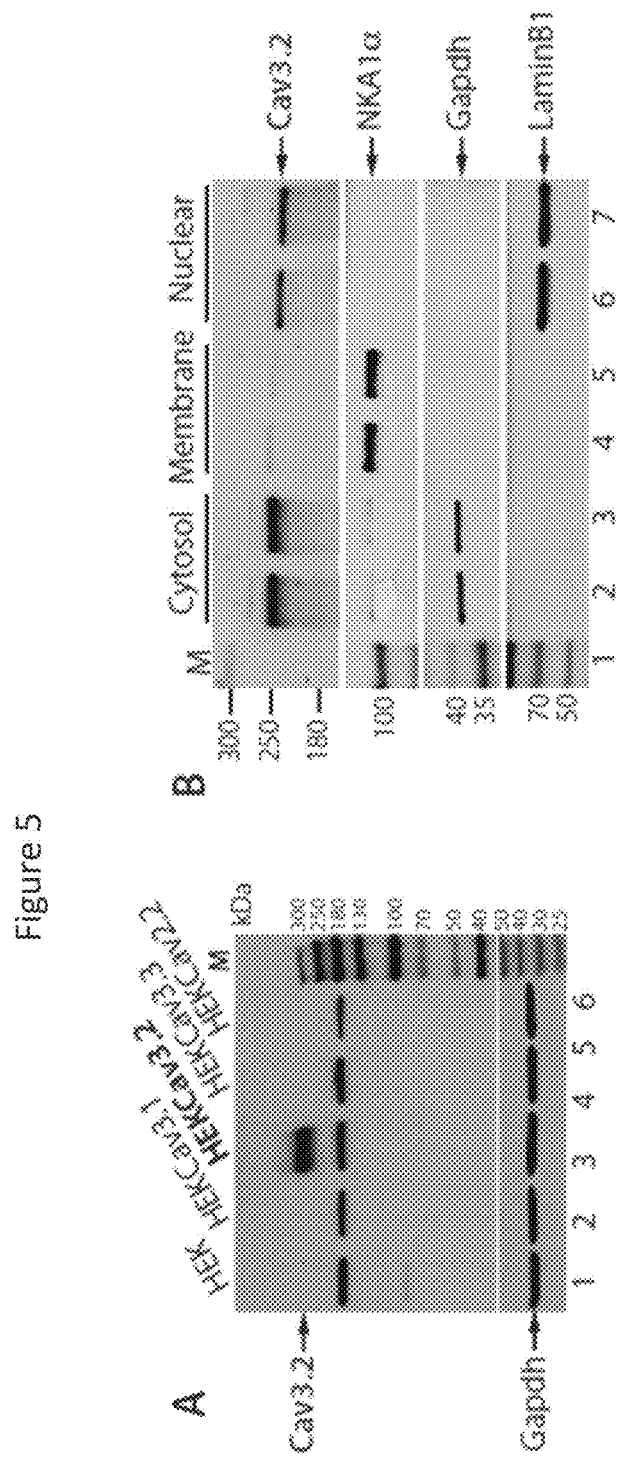

SEQUENCE LISTING

<160> NUMBER OF SEQ ID NOS: 6

<210> SEQ ID NO 1
<211> LENGTH: 17
<212> TYPE: PRT
<213> ORGANISM: Artificial Sequence
<220> FEATURE:
<223> OTHER INFORMATION: Synthetic-CaV3.2 inhibitory peptide aptamer iPA1

<400> SEQUENCE: 1

Arg Arg Ser Ser Trp Asn Ser Leu Gly Arg Ala Pro Ser Leu Lys Arg
1               5                   10                  15

Arg

<210> SEQ ID NO 2
<211> LENGTH: 22
<212> TYPE: PRT

```
<213> ORGANISM: Artificial Sequence
<220> FEATURE:
<223> OTHER INFORMATION: Synthetic-CaV3.2 inhibitory peptide aptamer
      iPA2

<400> SEQUENCE: 2

Arg Arg Arg Glu Glu Lys Arg Leu Arg Arg Leu Glu Arg Arg Arg
1               5                   10                  15

Lys Ala Gln Arg Arg Pro
            20

<210> SEQ ID NO 3
<211> LENGTH: 18
<212> TYPE: PRT
<213> ORGANISM: Artificial Sequence
<220> FEATURE:
<223> OTHER INFORMATION: Synthetic- CaV3.2 inhibitory peptide aptamer
      iPA3

<400> SEQUENCE: 3

Lys Arg Arg Ser Leu Arg Leu Tyr Ala Arg Trp Gln Ser Arg Trp Arg
1               5                   10                  15

Lys Lys

<210> SEQ ID NO 4
<211> LENGTH: 22
<212> TYPE: PRT
<213> ORGANISM: Artificial Sequence
<220> FEATURE:
<223> OTHER INFORMATION: Synthetic-CaV3.2 inhibitory peptide aptamer
      iPA4

<400> SEQUENCE: 4

Arg Gly Arg Ala Ser Glu Leu Glu Pro Ala Leu Gly Ser Arg Arg Lys
1               5                   10                  15

Lys Lys Met Ser Pro Pro
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic- CaV3.2  NP

<400> SEQUENCE: 5

Pro Ala Ala Pro Val Arg Ala Ser Pro Ala Ser Pro Gly Ala Pro Gly
1               5                   10                  15

Arg Glu Glu Gln
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic- Linker

<400> SEQUENCE: 6

Gly Leu Arg Ser Arg Ala Gln Ala Ser Asn Ser Ala Val Asp Gly Thr
1               5                   10                  15

Ala Gly Pro Gly Ser
            20
```

CALCIUM CHANNEL 3.2 INHIBITORY PEPTIDES AND USES THEREOF

CROSS-REFERENCE TO RELATED APPLICATIONS

This application claims priority to U.S. Provisional Application No. 63/216,032 filed on Jun. 29, 2021, the contents of which are incorporated by reference in its entirety.

STATEMENT REGARDING FEDERALLY SPONSORED RESEARCH

This invention was made with government support under R33NS116203 awarded by NIH. The government has certain rights in the invention.

SEQUENCE LISTING

This application is being filed electronically via EFS-Web and includes an electronically submitted Sequence Listing in .txt format. The .txt file contains a sequence listing entitled "650053.00883_ST25.txt" created on Jun. 29, 2022 and is 2,151 bytes in size. The Sequence Listing contained in this .txt file is part of the specification and is hereby incorporated by reference herein in its entirety.

BACKGROUND

Chronic pain is a devastating problem. Opioid treatment of chronic pain has numerous risks, including misuse, overdose, and addiction, highlighting the need for new analgesic targets and strategies. The peripheral nervous system (PNS) is a particularly accessible site for devising new pain treatments, since the primary sensory neurons (PSNs) of the dorsal root ganglia (DRG) initiate nociception and have a central role in the development and maintenance of nerve-injury painful neuropathy. PNS T-type calcium channels 3.2 (Cav3.2) regulate neuronal excitability and are a promising target for treatment of pain, but the development of selective inhibitors for peripheral action has proved elusive. Small peptides, especially those derived from the natural proteins as functionally interfering peptide aptamers (iPAs), are recognized as being highly effective and selective, allowing blockade of specific nociceptive molecular pathways. Their sustained expression in the PSNs encoded by AAV is a safe and feasible path to opioid- and addiction-free chronic pain treatment.

Molecular signaling interactions are often mediated by the regions of proteins lacking a defined tertiary structure, known as the intrinsically disordered regions (IDRs) that comprise a large part of the eukaryotic proteome and have been established as key facilitators of protein regulatory functionality. IDRs are also common in integral membrane proteins, particularly in the intracellular loops linking transmembrane structure domains and termini. These regions are intrinsically unstructured and often contain protein modulating architectures consisting of multiple domains existing as short linear peptide motifs within IDRs and functioning without a stable three-dimensional structure. This type of protein domains within IDRs is named as intrinsically disordered domains (IDDs), which are important players in multiple signaling regulations by engaging in binding to multiple partners and are considered as new and very promising drug targets.

The Cav3.2 channels encoded by Cacna1h and abundantly expressed in PSNs regulate sensory neuronal excitability and nociceptive transmission, and are an important target of non-opioid analgesics. Ample data support a prominent role of Cav3.2 in generating pain states, including elevated expression and activity in inflammatory pain, neuropathic pain, diabetic peripheral neuropathic pain, chemotherapy-induced peripheral neuropathy, osteoarthritis pain, and post-surgical pain, as well as itch. Since Cav3.2 is also expressed throughout the body, including endocrine, muscle, and kidney tissues, peripheral motor neurons, and pacemaker cells of the heart, efforts to date using currently available drugs administered systemically have led to inadequate analgesia and significant side effects. Indeed, recent multicenter, double-blind, controlled and randomized clinical trials using the established T-type channels blocker ethosuximide (Zarontin, Pfizer) or the T-type calcium channel blocker ABT-639 were terminated due to the high number of adverse events, as well as failure to reduce pain.

Thus, development of orally administered small molecule drugs targeting Cav3.2 channels has been hampered by lack of specificity contributing to significant off-target side effects. Accordingly, it would be beneficial to develop compositions and therapeutic methods that overcome the deficiencies of standard pain management protocols and provide new treatment paradigms for treating chronic pain while mitigating adverse or off-target side effects associated with conventional pain treatments. An unmet need exists for compositions and methods to achieve the aforementioned goals.

SUMMARY

The present disclosure overcomes the aforementioned drawbacks by providing compositions and methods as described herein.

In a first aspect, provided herein is an inhibitory polypeptide (e.g., peptide aptamer) as described in this disclosure which binds with high affinity to a Cav3.2 T-type calcium channel. In some embodiments, the peptide aptamer binds a Cav3.2 T-type calcium channel and inhibits a function(s) of the Cav3.2 T-type calcium channel. In some embodiments, the peptide aptamer specifically binds the Cav3.2 T-type calcium channel. In some embodiments, the Cav3.2 T-type calcium channel is a human Cav3.2 T-type calcium channel. In some embodiments, the peptide aptamer further comprises a scaffold or tag, such as, e.g., a peptide tag known in the art and/or described herein. In some embodiments, the peptide aptamer comprises or consists of the amino acid sequence of any one of SEQ ID NOs: 1-4 or a sequence having at least 85%, at least 90%, at least 95%, at least 98% sequence identity to SEQ ID NOs: 1-4 and are capable of binding and/or inhibiting the Cav3.2 T-type calcium channel.

In a further aspect, provided herein is an inhibitory polypeptide as described in this disclosure comprising two or more peptide aptamers which bind to a Cav3.2 T-type calcium channel. In some embodiments, the polypeptide binds a Cav3.2 T-type calcium channel and inhibits a function(s) of the Cav3.2 T-type calcium channel. In some embodiments, the polypeptide specifically binds the Cav3.2 T-type calcium channel. In some embodiments, the Cav3.2 T-type calcium channel is a human Cav3.2 T-type calcium channel. In some embodiments, the polypeptide comprises the amino acid sequence of any one of SEQ ID NOs: 1-5.

In another aspect, provided herein is a nucleic acid encoding the one or more inhibitory polypeptides (e.g. peptide aptamers), such as, e.g. a nucleic acid encoding a peptide aptamer or polypeptide as described in this disclosure. In some embodiments, the nucleic acid is a nucleic acid construct comprising a promoter sequence and a nucleic acid encoding a peptide aptamer described herein. In some embodiments, the nucleic acid construct is a vector, such as, e.g., an expression vector and/or viral vector. In some embodiments, the nucleic acid construct is an adeno-associated virus (AAV) vector.

In another aspect, provided herein is an adeno-associated virus (AAV) vector comprising or consisting essentially of a heterologous nucleic acid sequence operably linked to regulatory sequences which direct expression of a product from the heterologous nucleic acid sequence in a host cell, wherein the expression product of the heterologous nucleic acid sequence comprises one or more Cav3.2 inhibitory polypeptides described herein. The expression product of the heterologous nucleic acid sequence can comprise an amino acid sequence set forth in Table 1 or a portion thereof. The expression product of the heterologous nucleic acid sequence can comprise SEQ ID NO:1. The vector can be AAV type 1, AAV type 2, AAV type 3, AAV type 4, AAV type 5, AAV type 6, AAV type 7, AAV type 8, AAV type 9, AAV type 10, or AAV type 11.

In another aspect, provided herein is a pharmaceutical composition comprising the inhibitory polypeptides, constructs, or AAV vector as described in this disclosure, and a pharmaceutically acceptable carrier.

In a further aspect, provided herein is a method of treating pain in a subject in need thereof. The method can comprise or consist essentially of administering to the subject a therapeutically effective amount of an AAV vector comprising a heterologous nucleic acid sequence operably linked to regulatory sequences which direct expression of a product from the heterologous nucleic acid sequence in a host cell, wherein the expression product of the heterologous nucleic acid sequence comprises one or more Cav3.2 inhibitory peptide aptamers. In some cases, administering comprises targeted delivery to a dorsal root ganglion (DRG) of the subject, whereby expression of the product comprising one or more Cav3.2 inhibitory peptide aptamers partially or fully inhibits Cav3.2 T-type calcium channel activity in the DRG.

In another aspect, provided herein is a method of treating pain in a subject in need thereof. The method can comprise or consist essentially of administering to the subject a therapeutically effective amount of an AAV particle comprising an AAV vector genome comprising or encoding one or more Cav3.2 inhibitory peptide aptamers. Administering can comprise injecting a therapeutically effective amount of the AAV particles into a dorsal root ganglion of the subject. Expression of said one or more Cav3.2 inhibitory peptide aptamers can reduce nociceptive dorsal root ganglion (DRG) neuron excitation. The pain can be chronic pain or neuropathic pain.

In a further aspect, provided herein is a method of treating pain in a subject. The method can comprise or consist essentially of administering to a dorsal root ganglion of the subject an effective amount of a Cav3.2 T-type calcium channel inhibitor. The Cav3.2 T-type calcium channel inhibitor can be a polypeptide. The Cav3.2 T-type calcium channel inhibitor can inhibit sensory neuron excitation. The Cav3.2 T-type calcium channel inhibitor can inhibit nociceptive dorsal root ganglion (DRG) neuron excitation. The pain can be chronic pain or neuropathic pain.

BRIEF DESCRIPTION OF THE DRAWINGS

This patent or patent application file contains at least one drawing in color. Copies of this patent or patent application publication with color drawings will be provided by the Office upon request and payment of the necessary fee.

T-type calcium currents were elicited from −110 to +60 mV in 10 mV increments. The external solution was in mM: 151 TEA-Cl, 2 CaCl2, 1 MgCl2, 10 HEPES, 13 Glucose, pH=7.4. The internal solution was in mM: 125 CsCl, 10 NaCl, 1 MgCl2, 10 EGTA, 10 HEPES, pH=7.2. Representative T-type calcium currents recorded from Sham (HEK3.2 cells) (A), and from HEK3.2 cells transfected with 5 mM plasmid containing GFP (B), GFP-3.2NP (C), GFP-3.2iPA1 (D), and GFP-3.2iPA2 (E). F) IV curves for T-type calcium currents recorded from Sham (open circles, black), GFP (filled circles, green), GFP-3.2NP (triangles, green), GFP-3.2iPA1 (triangles, green), and GFP-3.2iPA2 (diamonds, green). G) Peak T-type calcium currents for sham cells (45.1±4.3 pA/pF, n=18), GFP (45.4±4.0 pA/pF, n=8), GFP-3.2NP (41.1±3.3 pA/pF, n=8), GFP-3.2iPA1 (20.2±2.0 pA/pF, n=14), and GFP-3.2iPA2 (11.8±1.7 pA/pF, n=14). H)

Activation curves (G/Gmax). Sham (V1/2=−52.4±1.1 mV, n=18), GFP (V1/2=−51.7±1.8 mV, n=8), GFP-3.2NP (V1/2=−54.1±2.7 mV, n=8), GFP-3.2iPA1 (V1/2=−56.1±1.4 mV, n=14), GFP-3.2iPA2 (V1/2=−54.6±1.4 mV, n=14). I) Inactivation curves (I/Imax). Sham (V1/2=−66.2±0.7 mV, n=18), GFP (V1/2=−64.1±1.1 mV, n=8), GFP-3.2NP (V1/2=−64.9±1.5 mV, n=8), GFP-3.2iPA1 (V1/2=−69.8±1.7 mV, n=14), GFP-3.2iPA2 (V1/2=−68.8±2.1 mV, n=14) *p<0.05, one-way ANOVA followed by Tukey's post hoc comparison.

Figure 4:
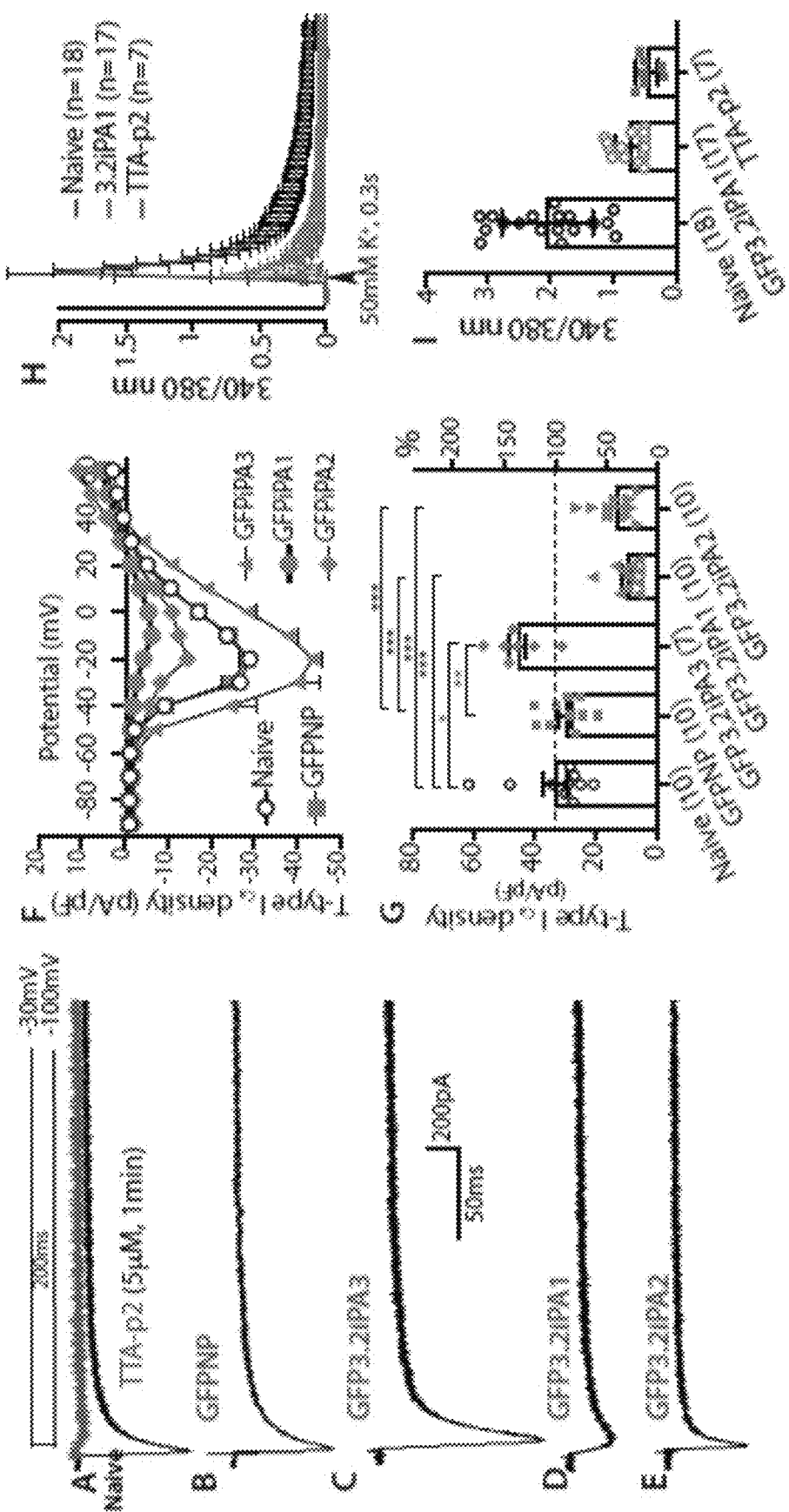
Figure 4:
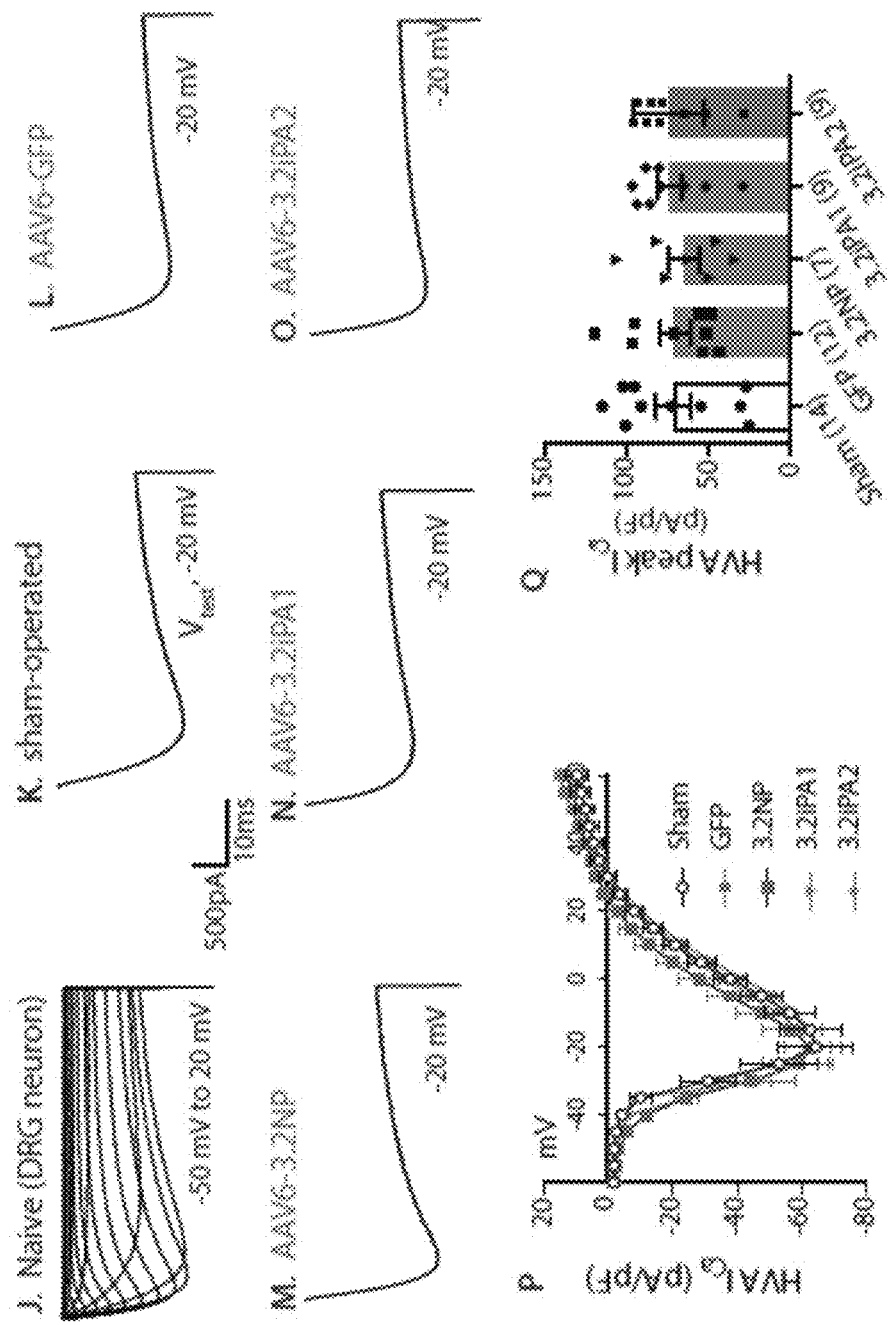

FIG. 4. Inhibition of LVA-$I_{Ca}$ but not HVA-$I_{Ca}$ by Cav3.2iPA (DRG neurons). AAV6-encoding GFPCav3.2iPA1 (GFP3.2iPA1), GFPCav3.2iPA2 (GFP3.2iPA2), GFPCav3.2iPA3 (GFP3.2iPA3), and control of GFP3.2NP (GFPNP), were generated and injected into L4/L5 DRG of naïve rats. Shown are the results of whole-cell T-type $I_{ca}$ recordings on DRG dissociated neurons 4-week post vector injection. (A-E) are typical traces of T-type $I_{Ca}$ of neurons (20-40 μm in diameter) from a naïve rat (A, blocked by 5 μM TTA-p2), and rats injected with AAV-GFPNP (B), GFP3.2iPA3 (C), GFP3.2iPA1 (D), and GFP3.2iPA2 (E). Recording protocol was shown on the top of panel A. Comparison of corresponding mean peak current density-voltage (I/V) relationship from different constructs as indicated (F) and quantitative analysis of averaged peak T-type current (T-$I_{Ca}$) density (G). (H, I) AAV-mediated 3.2iPA1 expression in PSNs significantly decrease $[Ca^{2+}]_c$. Depolarization by 0.3 s of 50 mM $K^+$ increased $[Ca^{2+}]_c$ which is blocked by TTA-p2 in the PSNs of naïve rats and this effect was blocked by AAV-mediated 3.2iPA1 expression in PSNs. *p<0.05, p<0.01, and *p<0.001, one-way ANOVA followed by Tukey post hoc multiple comparisons. Patch-clamp recordings showed no effect of GFP3.2iPA1 and GFP3.2iPA2 on peak HVA $I_{Ca}$ (J-Q).

Figure 5:
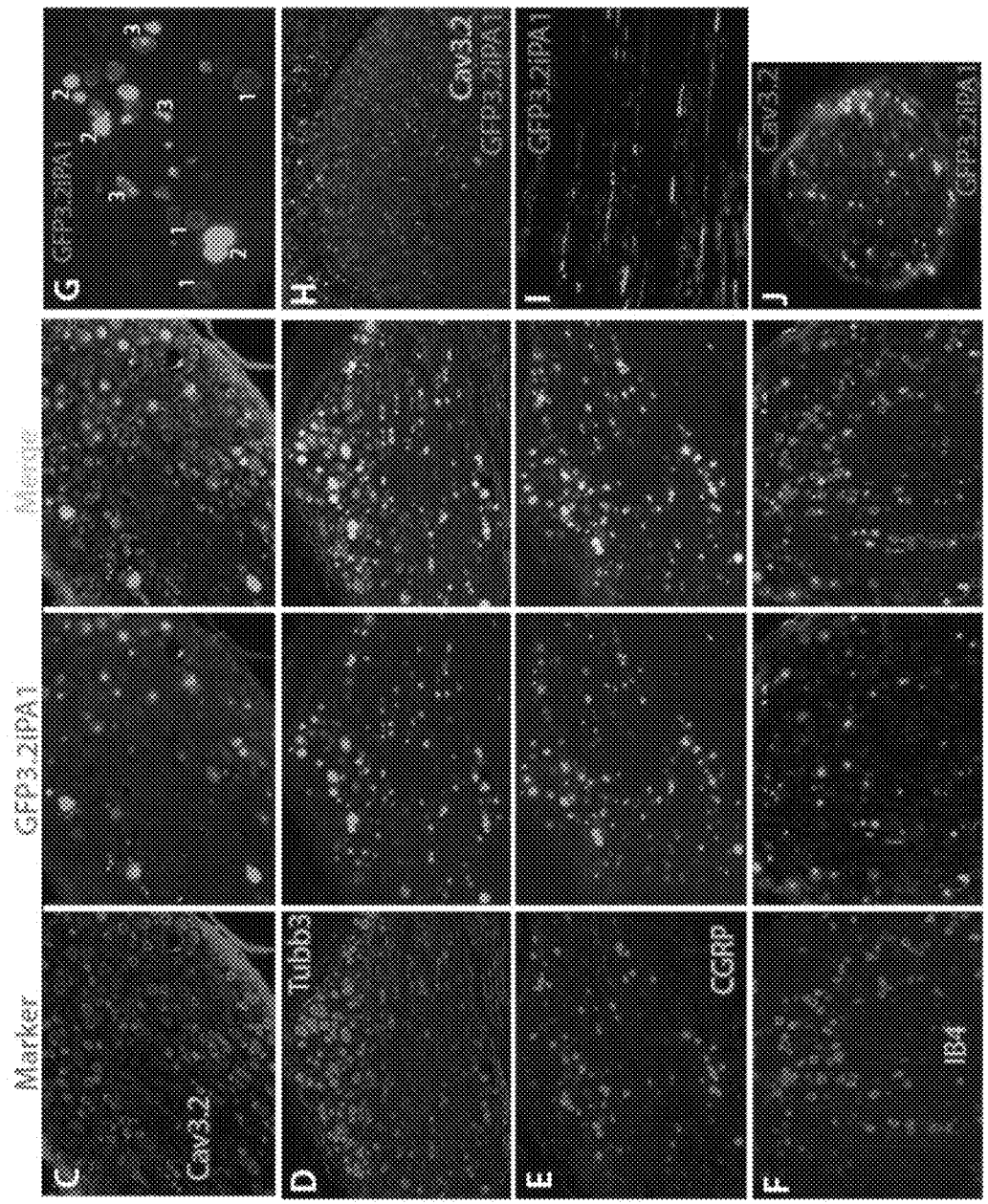

FIG. 5. Detection of $Ca_v3.2$ expression. (A) Western blots verify that $Ca_v3.2$ antibody specifically detects $Ca_v3.2$ but not other T-type isoforms nor $Ca_v2.2$, and (B) $Ca_v3.2$ multiple cellular localization (cytosol, membrane, and nuclear) prepared from DRG of naïve rats. (C-F) Representative IHC montage images of GFP-$Ca_v3.2$iPA expression (green), colabeled with $Ca_v3.2$ (C, red), Tubb3 (D, red), IB4 (E, red), and CGRP (F, red), in L5-DRG of TNI rats 5 weeks after AAV6-3.2iPA1 treatment. (G) A representative IHC images of DRG section shows multiple cellular localization of GFP-$Ca_v3.2$iPA in PSNs, with 1, 2, and 3 denote the patterns of localization in membrane, cytosol, and nuclear, respectively). (H-J) Representative IHC images show GFP-Cav3.2iPA expression (green), colabeled with $Ca_v3.2$ (red), in the neuropil of ipsilateral spinal dorsal horn (H); in sciatic nerve (I); and afferent terminals (J), colabeled with IB4 (red), within the dermis of ipsilateral hindpaw. Scale bar: 50 μm for all images.

Figure 6:
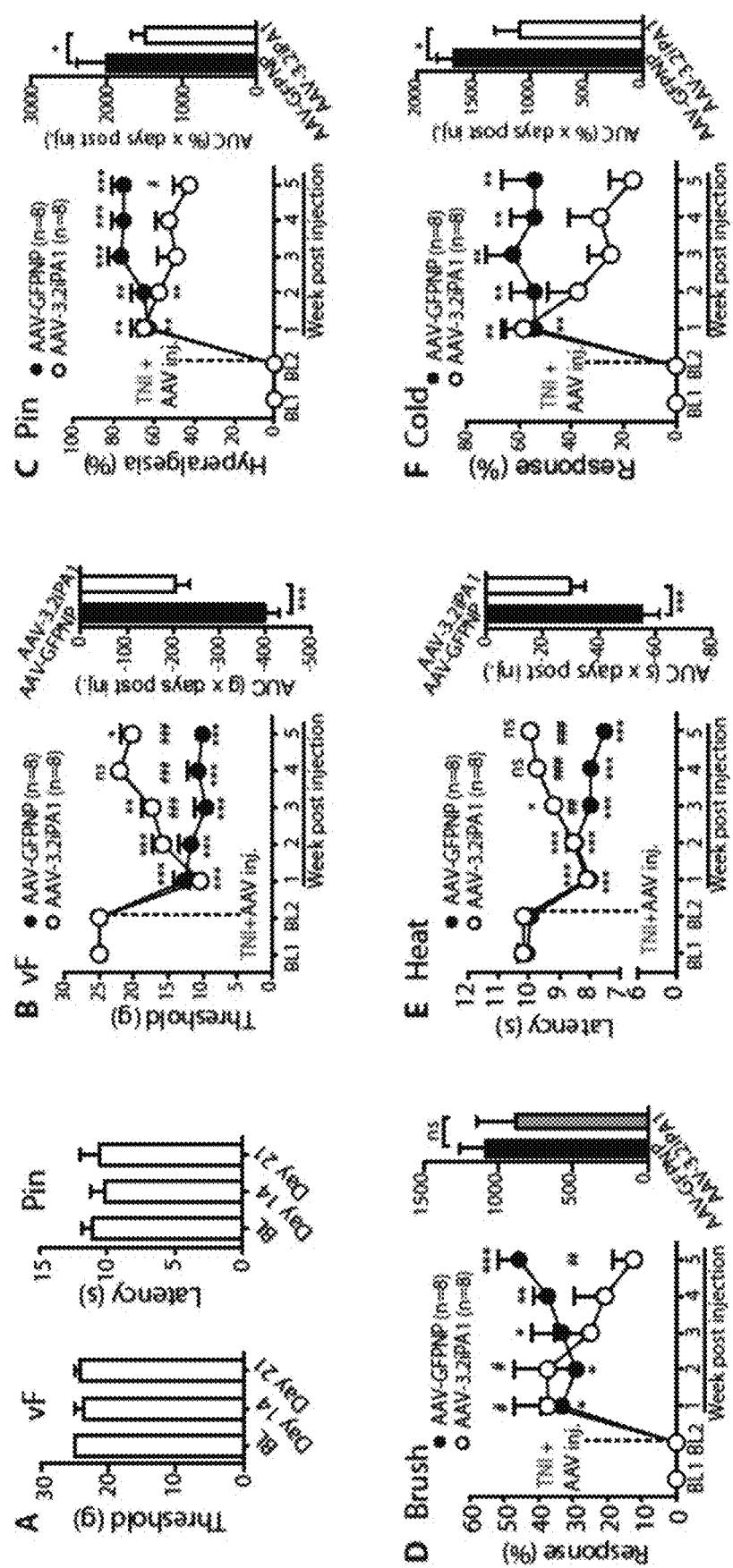

FIG. 6. Attenuation of TNI-induced hypersensitivity by AAV6-GFPCa$_v$3.2iPA1 treatment. Panel A evaluates sensory sensitivity to innocuous punctate mechanical stimulation (von Frey, left) and to heat stimulation (right) at baseline and day 28 after AAV6-GFPCav3.2iPA1 (AAV6-3.2iPA1) injection in uninjured rats (n=4). Left panels of B-F show the time courses for the group averages of sensitivity to von Frey (B), hyperalgesia behavior after touch with a pin (Pin, C), dynamic brush (D), sensitivity to heat (E), and acetone stimulation (Cold, F), before TNI and after DRG injection of either AAV6-GFPsc (filled circle, n=8 rats) or AAV6-3.2iPA1 (empty circles, n=8 rats). Injection of AAV vectors into the fourth and fifth lumbar DRG was performed immediately after the procedure of TNI, denoted by arrowheads. #p<0.05, ##p<0.01, and ###p<0.001 for comparison to BL and *p<0.05, p<0.01, and *p<0.001 for comparison between groups after treatment, respectively (B and E, repeated measures two-way ANOVA and Bonferroni post-hoc; c, d and f, nonparametric analyses by Friedman's test with Dunn's post-hoc). Right panels of B-F show averaged area under the curve (AUC) calculated for each individual for the time period following vector injection. *p<0.05, and ***p<0.01 for AUC comparison between groups (unpaired, two-tailed Student's t tests).

Figure 7:
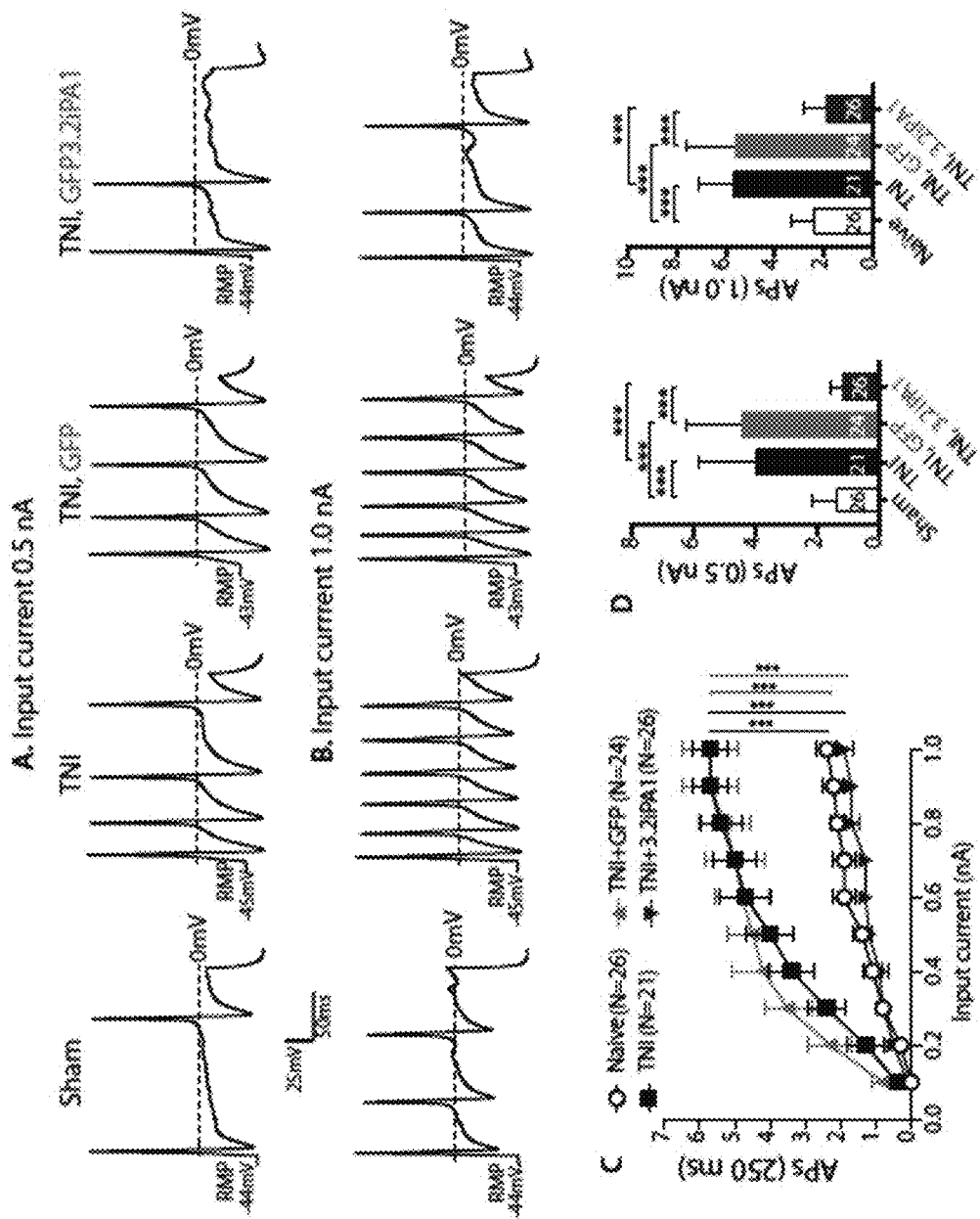

FIG. 7. Current-clamp analysis of AAV6-3.2iPA1 transduction on DRG neuron excitability. Representative action potential (AP) traces elicited by 250 ms depolarizing current of 0.5 nA (A) and 1.0 nA (B) (same cells) from resting membrane potentials (RMP) were recorded from DRG neurons dissociated from the rats of sham, TNI, and TNI treated with AAV6-GFPNP or AAV6-3.2iPA1, as indicated. Comparison of responses (number of APs evoked by a 250 ms stimulus) for the populations of DRG neurons in different groups across a range of step current injections from 0.1 to 1.0 nA (C), two-way ANOVA of main effects of groups with Bonferroni post-hoc, *p<0.001. The bar charts show analysis of AP numbers evoked by input current at 0.5 nA (D, left) and 1.0 nA (right) from resting membrane potentials (RMP), respectively. The number in each bar is the number of analyzed neurons per group. *p<0.001, one-way ANOVA analysis of variance with Turkey post-hoc.

Figure 8:
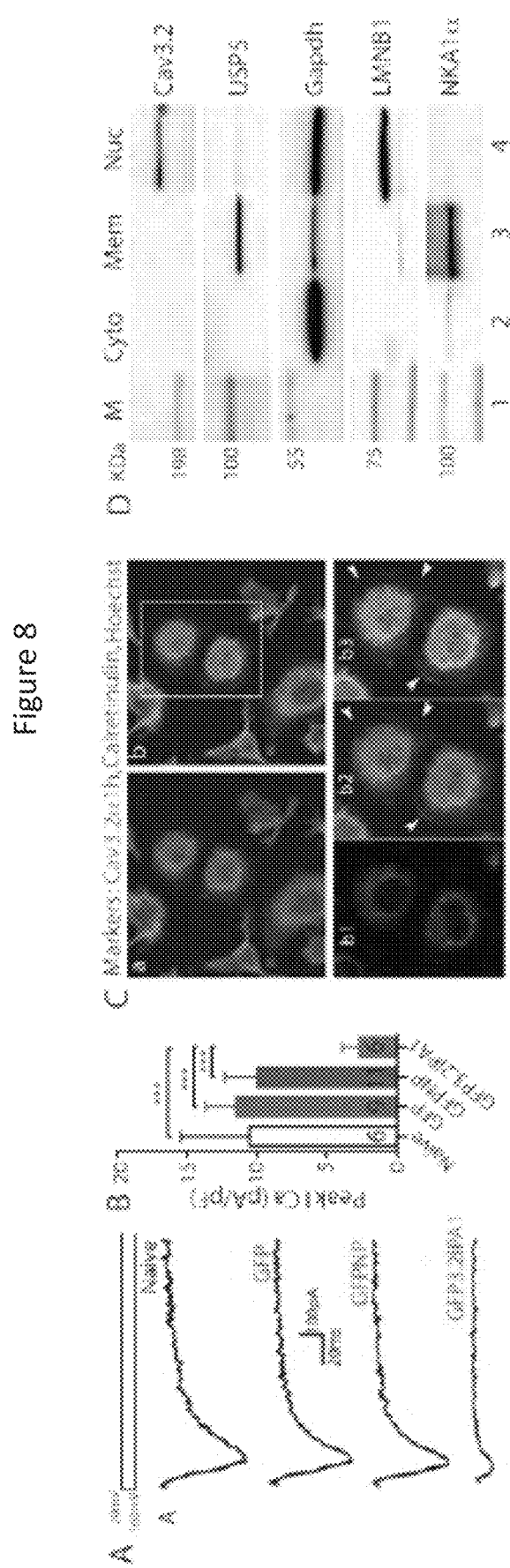

FIG. 8. GFP3.2iPA1 inhibits CaV3.2 current in NG-108 cells. Representative T-current traces (A, Vh=−100 mV and test-20 mV) and peak ICa (B) in naïve, GFP-, GFP3.2NP- and GFP3.2iPA1-transfected NG-108 cells (number in each bar is the cells recorded). Mean±SEM, ***p<0.001, one-way ANOVA and Turkey post hoc. CaV3.2 is expressed in NG108 cells with multiple cellular localization (Ca, b). Inset in panel b is magnified and shown as montage images (b1-b3) displaying CaV3.2 IR signals localized in cell membrane (b2 and b3, arrowheads) and endoplasmic reticulum (ER). CaV3.2 is detected in nucleus upon western blots (D).

Figure 9:
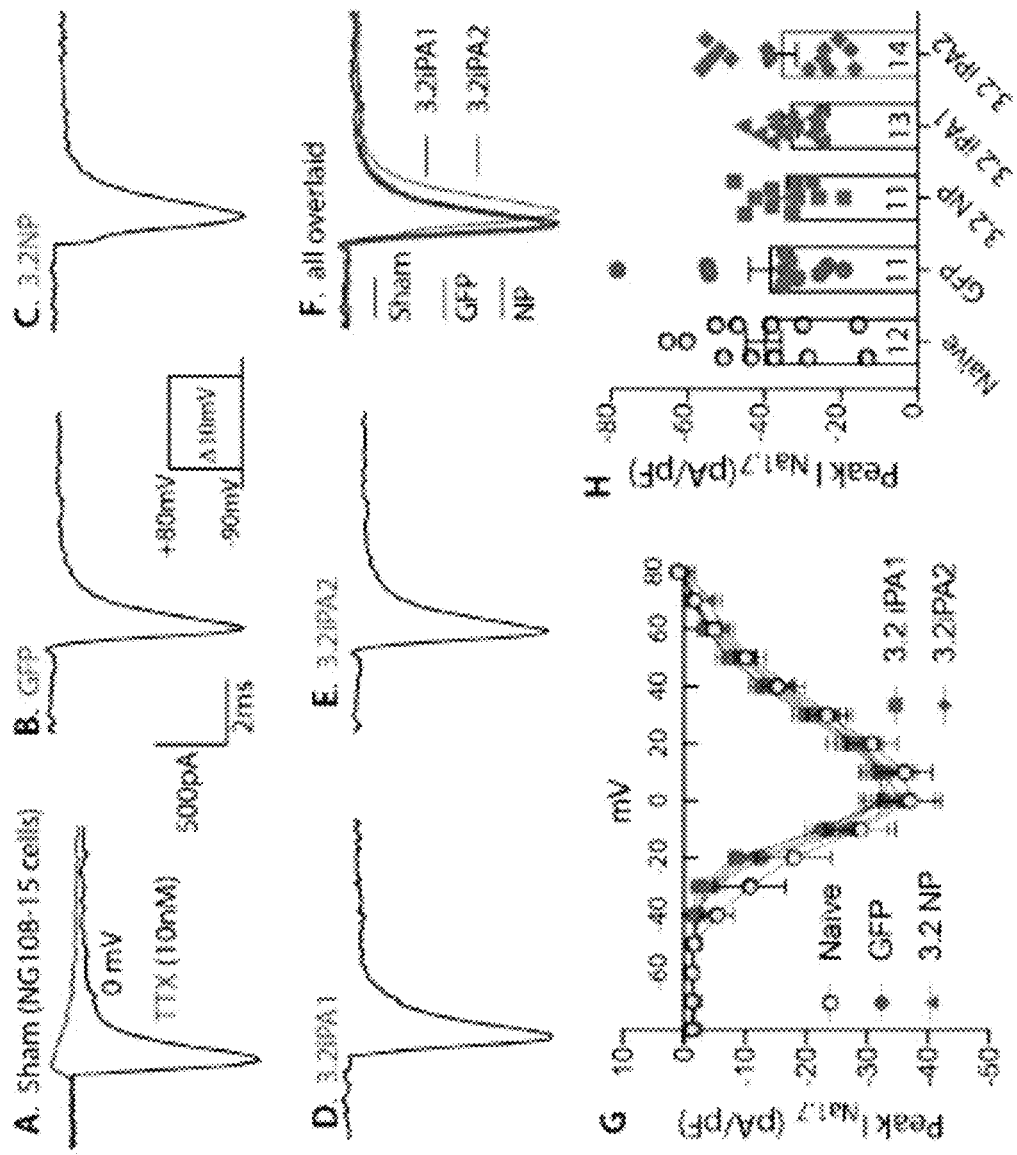

FIG. 9. No effect on Nav1.7 current (INa1.7) of Cav3.2iPAs transfected to neuronal NG108-15 cells. Shown are the results of whole-cell INa1.7 patch-clamp recording of NG-108-15 (NG108) cells in non-differentiation culture after transfection. (A-F) are reprehensive currents (single traces at 0 mV) of sham-transfection showing the current is blocked by 10 nM of TTX in bath solution (A) or NG108 cells transfected with GFP (B), GFP3.2NP (C), GFP-3.2iPA1 (D), GFP-3.2iPA2 (E), and the merged currents of A-E shown in (F). Currents were elicited by 20 ms depolarizing voltage steps to +80 mV from a Hv −90 mV (insets: recording protocol and current/time scales). Comparison of corresponding averaged peak INa1.7 density-voltage (I/V) relationship from different constructs as indicated (G) and quantitative analysis of averaged peak INa1.7 density show no significant effect of different constructs as indicated on INa1.7 (H); p>0.05 for multiple comparison of peak INa1.7 in different groups; One-way ANOVA followed by Tukey post hoc multiple comparisons.

Figure 10:
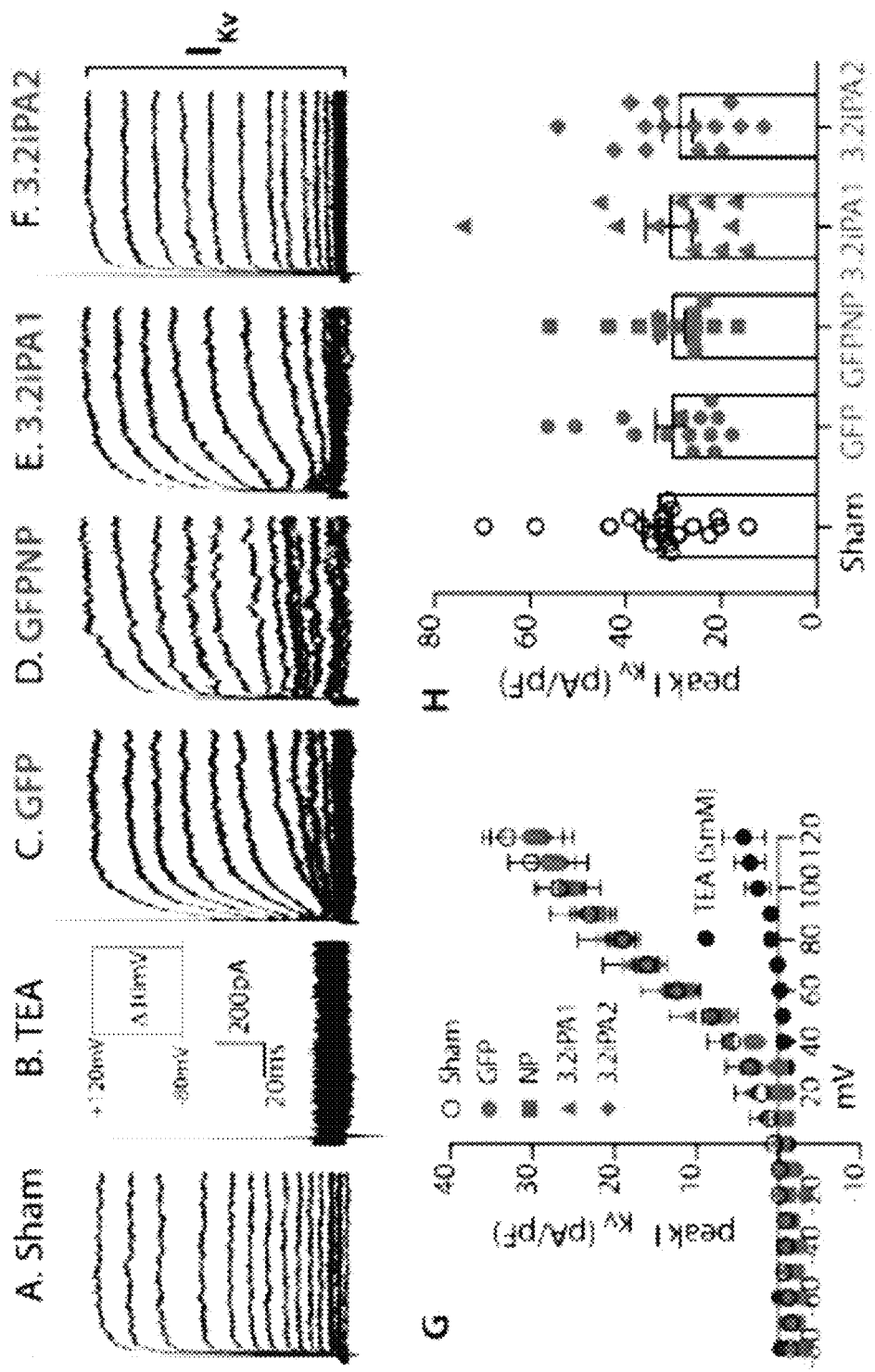

FIG. 10. No effect of Cav3.2iPAs on current of voltage-gated potassium channels (IKv) in neuronal NG108-15 cells. Shown are the results of whole-cell IKv recording on NG-108-15 (NG108) cells in non-differentiation culture after transfection. (A-F) Representative IKv of NG108 cells with sham-transfection (A) and IKv defined by outward currents blocked by Kv blocker Tetraethylammonium (TEA, 5 mM) (B) or NG108 cells transfected with the plasmid expressing GFP (C), GFPNP (D), GFP-Cav3.2iPA1 (3.2iPA1) (E) and GFP-Cav3.2iPA2 (3.2iPA2) (F) (insets:

recording protocol and current/time scales). Currents were elicited by 10 ms depolarizing voltage steps to +120 mV from a Hv −80 mV. Comparison of corresponding averaged peak IKv density-voltage (I/V) relationship (G) and quantitative analysis of averaged peak IKv density (H) show no significant effect of different constructs as indicated on IKv; p>0.05 for multiple comparison of peak IKv in different groups; One-way ANOVA followed by Tukey post hoc multiple comparisons.

DETAILED DESCRIPTION

All publications, including but not limited to patents and patent applications, cited in this specification are herein incorporated by reference as though set forth in their entirety in the present application.

In General

The inhibitory polypetides, compositions and methods provided herein are based at least in part on the inventors' development of linear peptide sequences that function as inhibitory polypeptides or inhibitory peptide aptamers (iPAs) to provide highly effective and selective blockade of Cav3.2 T-type calcium channel function. The linear peptide sequences were identified by in silico exploration and analysis of the intracellular II-III linker and C-terminus of the native Cav3.2 protein. As described herein, targeted delivery to the dorsal root ganglia (DRG) using viral constructs, e.g., adeno-associated viral vectors provides for sustained expression of these iPAs in the peripheral nervous system as improved methods of chronic pain treatment with minimal off-target effects. Moreover, the Cav3.2 inhibitory peptide aptamers described herein are advantageous for screening for small molecules that can inhibit 3.2 T-type channel activity and treat pain.

Advantages of the inhibitory polypeptides, compositions and methods provided herein for targeted blockade of nociceptive DRG neuron excitation are multifold and include, without limitation, (1) high transduction efficiency, including expression in neuronal somata as well as their central and peripheral axonal terminals; (2) motor neurons are unaffected; (3) transgene expression is restricted to the targeted segmental level and side of injection; (4) the DRG is not harmed by injection in contrast to injections into peripheral nerves or the central nervous system (CNS); and (5) very low doses of vector, compared to intrathecal or systemic injection, are needed for highly efficient gene transfer, making clinical translation feasible at low cost, and minimizing neutralizing antibody formation.

Compositions

The present disclosure provides in a first aspect an inhibitory polypeptide comprising an amino acid sequence set forth in any one of SEQ ID NOs: 1-5, wherein the polypeptide binds specifically to a human Cav3.2 protein and inhibits human Cav3.2 protein function. In some embodiments, the inhibitory polypeptide comprises two or more amino acid sequences set forth in any one of SEQ ID NOs: 1-5 linked by a linker sequence.

The terms "inhibitor polypeptide", "inhibitory peptide", "peptide aptamer" and "inhibitory peptide aptamer" are used interchangeably herein to refer to small polypeptides (i.e. proteins) that are selected to bind to specific sites on their target molecules. Peptide aptamers are generally short linear peptides having a length of 5-20 amino acid residues. The inhibitory polypeptides or inhibitory peptide aptamers refers to peptides that function as decoy molecules to selectively interfere with the function of their target protein by preemptively binding to the proteins. In the present invention, the inhibitory polypeptides are capable of inhibiting CaV3.2 T-type calcium channel activity, reducing or inhibiting nociceptive DRG neuron excitation, or both.

As used herein, the term "peptide" is broadly defined to include any organic compound consisting of two or more amino acids joined by a chemical bond in which the amino group of one amino acid combines with the carboxyl group of a second amino acid. The term "polypeptide" refers to chain of amino acids but as used therein the term peptide and polypeptide may be used interchangeably to refer to the present invention. As used herein, the term "amino acid" is broadly defined to include naturally occurring amino acids as well as non-naturally occurring amino acids, including amino acid analogs and derivatives, such as molecules containing an amino acid moiety. As used herein, the term amino acid therefore embraces, for example, naturally occurring proteogenic L-amino acids; D-amino acids; chemically modified amino acids such as amino acid analogs and derivatives; naturally occurring non-proteogenic amino acids such as norleucine, β-alanine, ornithine, etc.; and chemically synthesized compounds having properties known in the art to be characteristic of amino acids.

In some aspects, the inhibitory polypeptides (e.g. SEQ ID NO:1-5) are engineered to be linked (e.g., displayed) on a protein scaffold or tag. Thus, in some aspects the inhibitory polypeptide comprises a tag or scaffold. The inhibitory polypeptide may be linked to the scaffold or tag by a linker. In some embodiments, the one or more inhibitory polypeptides are made as a fusion protein comprising the inhibitory polypeptide linked by a linker to a polypeptide scaffold or tag. In other words, the inhibitory peptide(s) are synthesized as part of the same polypeptide chain as the scaffold and are constrained at their N termini, C termini, or both to the scaffold or tag. In some embodiments, the inhibitory peptide(s) are attached at both the N and C termini to the scaffold or tag, decreasing the diversity of the conformations that the inhibitory polypeptide can adopt causing it to adopt a single conformation. In some embodiments, the inhibitory peptide aptamers can bind their targets tightly and can have high binding affinities (e.g. nM ranges).

Suitable protein scaffolds or tags are known in the art. For example, a peptide scaffold may be a known small, ordered, soluble protein or a rigid, compact, preferably monomeric, stable protein core capable of displaying iPA on its surface (see, e.g., Reverdatto, Sergey et al. "Peptide aptamers: development and applications." Current topics in medicinal chemistry vol. 15.12 (2015): 1082-101. doi:10.2174/1568026615666150413153143, incorporated by reference in its entirety). Thus, in some aspects, the inhibitory polypeptide is a fusion protein comprising the inhibitory polypeptide linked by a linker to a polypeptide scaffold or tag.

In some cases, a Cav3.2 inhibitory peptide aptamer appropriate for the methods provided herein can inhibit nociceptor excitation. Nociceptors are specialized sensory neurons (e.g., nociceptive dorsal root ganglion neurons) that have Aδ- and C-fibers in the peripheral nerve and sensory non-corpuscular "free nerve endings" in innervated organs. Nociceptors transduce mechanical, thermal, and chemical stimuli into a depolarizing sensor potential. If the depolarization is sufficiently large, it opens voltage-gated ion channels and triggers the generation of action potentials that are conducted to the dorsal horn of the spinal cord or the brainstem. In exemplary cases, a Cav3.2 inhibitory peptide aptamer appropriate for the methods provided herein inhibit nociceptive dorsal root ganglion (DRG) neuron excitation.

Figure 1:
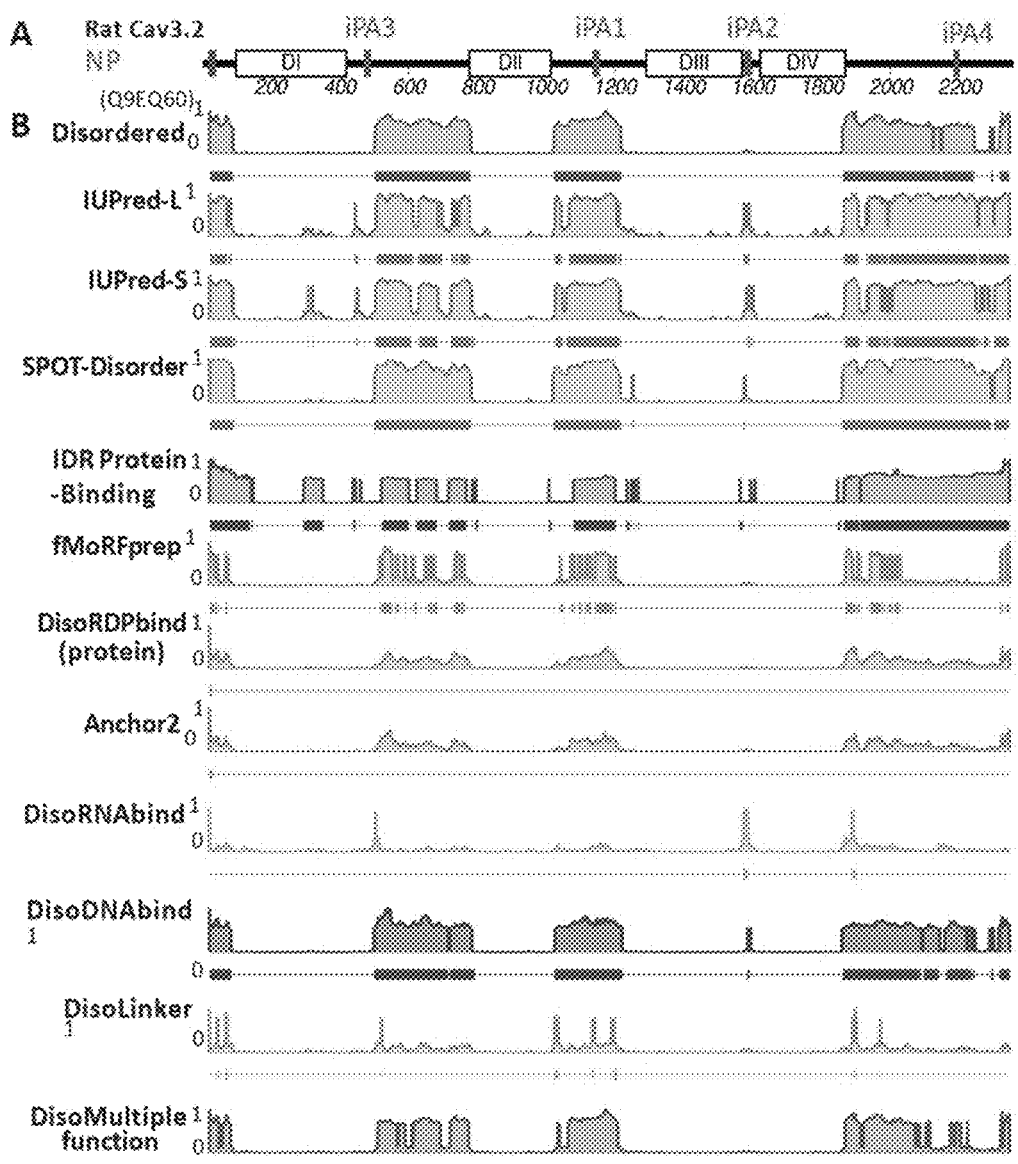
FIG. 1. In silico prediction of $Ca_v3.2$-IDRs and design of candidate $Ca_v3.2$iPAs. (A) Diagram of full length of $Ca_v3.2$ protein, with white boxes labeled DI-DIV as $Ca_v3.2$ transmembrane domain I-IV and the red bars within the sequences showing the position of the predicted iPAs. (B) IDRs predicted by DEPICTER (IUPred2A: Intrinsically unstructured Proteins, Anchor 2: Potential binding sites in disordered regions, SPOT-Disorder-Single: Accurate Single-Sequence Prediction of Protein Intrinsic DisorderfMoRF-pred: Fast Molecular Recognition Feature predictor, DisoR-DPbind: Predictor of disorder-mediated protein binding regions). (C) the phosphorylation sites (serine, threonine, and tyrosine) predicted by DEPP (Disorder enhanced phosphorylation prediction). (D) Composition of disordered aa in $Ca_v3.2$, compared to a number of nociception-related ion channels. (E) Five potential iPAs with their aa sequence, position in $Ca_v3.2$, IDR scores, and % of polybasic aa. (F) A map showing each component of an AAV plasmid coding GFP-iPA fusion and (G) GFP western blots of each designed construct after transfection to HEK cells, as indicated. (H) The crystal structure analysis of GFP-linker (left) and designed GFP3.2iPA1 (middle) by I-TASSER and prediction of disordered scores of GFP-iPA1, 2 (right). (I) Images (GFP, top; Phase, middle; and merged pictures, bottom) show cellular localization of each construct as indicated after transfection to HEK cells, scale bar: 25 μm for all.
Figure 1:
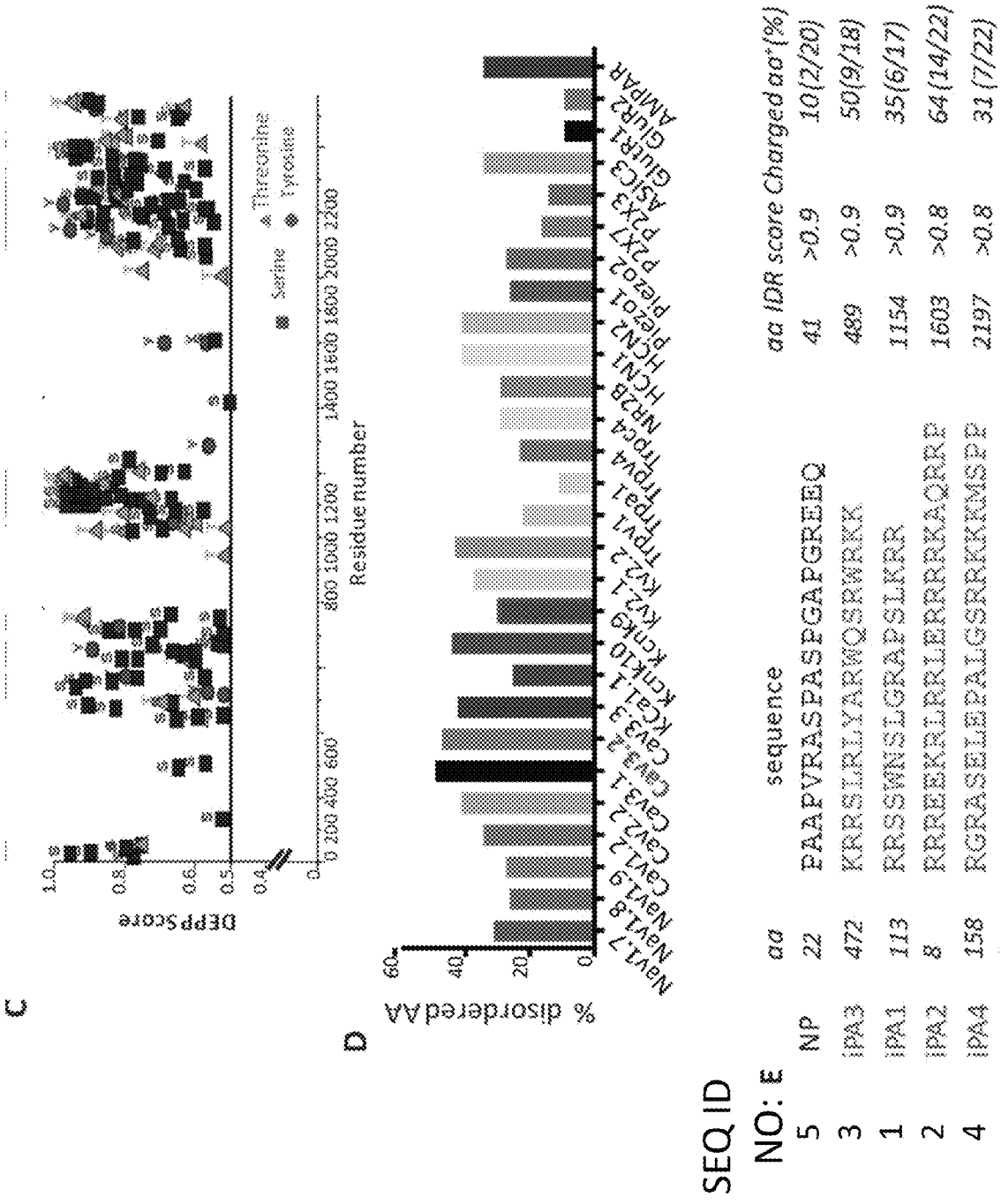
Figure 1:
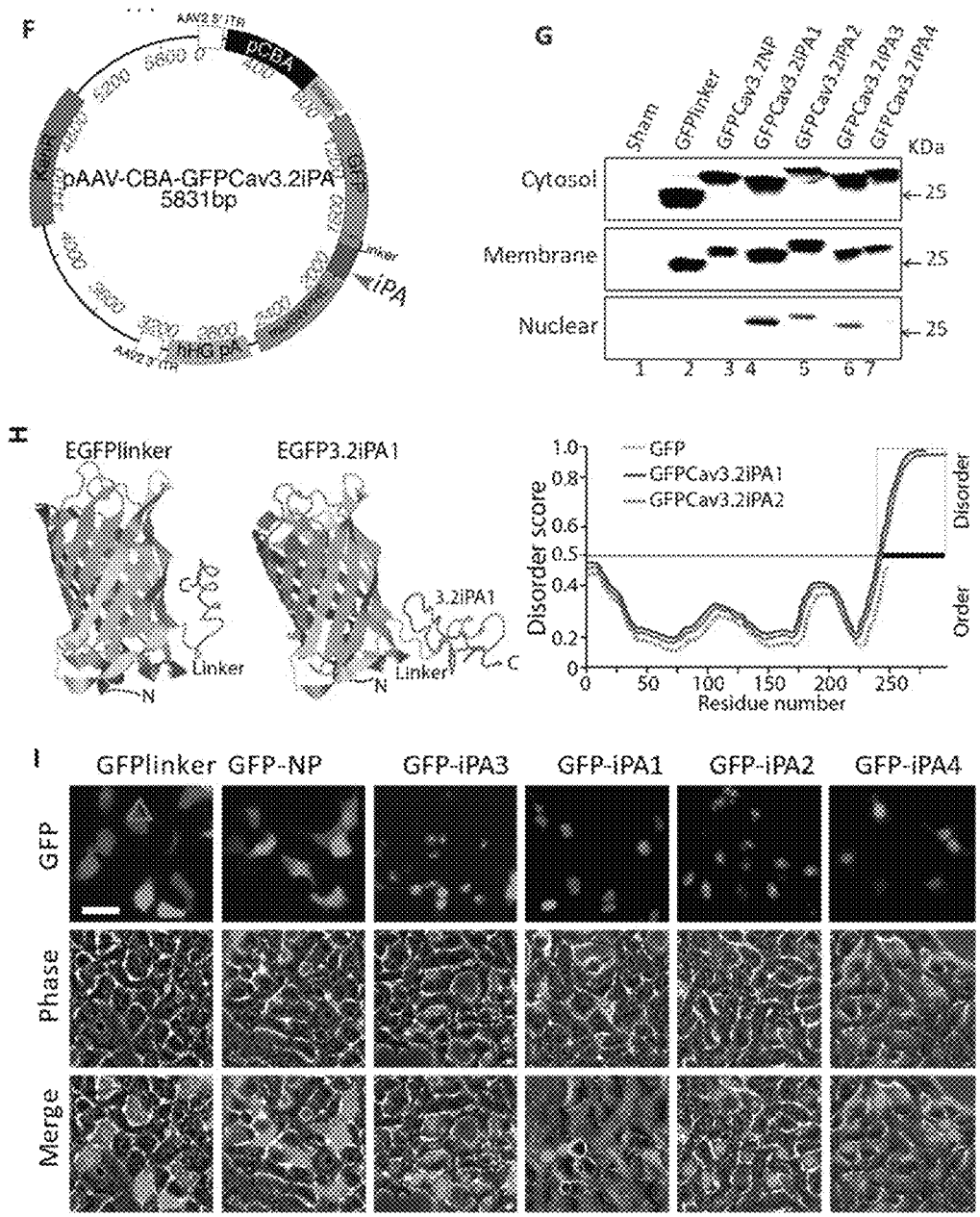

In some cases, Cav3.2 inhibitory peptide aptamers comprise polybasic peptides (PBPs) located within the intrinsically disordered regions (IDRs) of a Cav3.2 amino acid sequence. Exemplary peptides, referred to herein as "Cav3.2 intrinsically disordered peptides" or "Ca$_v$3.2IDPeps" include those set forth in FIG. 1. In Table 1, the underlined sequences show clusters of PBPs. In some cases, the Cav3.2 inhibitory peptide is a 17-mer peptide derived from a disordered and conserved region of a Cav3.2 intracellular linker region selected from I-II, II-III, III-V, and C-terminus. In some cases, the Cav3.2 inhibitory peptide is a 17-mer peptide derived from II-III linker (see FIGS. 4E, 4F)) having the amino acid sequence RRSSWNSLGRAPSLKRR (SEQ ID NO:1) or an amino acid sequence having at least 90% identity to SEQ ID NO:1. As demonstrated in the Examples, the 17-mer of SEQ ID NO:1 (corresponding to Cav3.2iPA1) acts as a potent T-type channel inhibitor both in vitro and in vivo.

TABLE 1

Cav3.21DPeps

| Name | Aa | Sequence | SEQ ID NO: |
|---|---|---|---|
| iPA1 | 1138-1154 | RRSSWNSLGRAPSLKRR | 1 |
| iPA2 | 1582-1603 | RRREEKRLRRLERRRRKAQRRP | 2 |
| iPA3 | 472-489 | KRRSLRLYARWQSRWRKK | 3 |
| iPA4 | 2176-2197 | RGRASELEPALGSRRKKKMSPP | 4 |
| NP | 22-41 | PAAPVRASPASPGAPGREEQ | 5 |

Accordingly, in a second aspect, provided herein is a construct encoding the inhibitory polypeptides described herein. In some aspects, provided herein in a construct for reducing or inhibiting nociceptive DRG neuron excitation. The constructs of the present invention include a nucleotide sequence encoding one or more Ca$_v$3.2 inhibitory peptide aptamers (e.g., SEQ ID NO: 1-5).

In some cases, the construct comprises a nucleic acid sequence encoding a single Ca$_v$3.2 inhibitory peptide aptamer such as a 17-mer peptide selected from sequences or portions thereof set forth in Table 1. In other cases, the construct comprises a nucleic acid encoding two or more Ca$_v$3.2 inhibitory peptide aptamers. The two or more inhibitory peptides can be of the same type or of different types.

In some cases, the construct comprises a nucleic acid sequence encoding a Ca$_v$3.2 inhibitory peptide that comprises one or more modifications. For example, the peptide can comprise a secretory signal. In other cases, the peptide comprises a detectable label such as a fluorophore, 5-carboxyfluorescein, radiolabel, green fluorescent protein (GFP) or a derivative thereof, or other detectable cargo. Other modifications appropriate for use with the peptide aptamers provided herein include, without limitation, glycosylations, acetylations, phosphorylations, as well as the addition of peptide linkers such as a cysteine linker or spacer. Peptide modifications can occur at the N-terminal and/or C-terminal ends of a peptide. For example, the amino and/or carboxy termini of a peptide can be modified produce other compounds of the invention.

As used herein, the term "construct", "nucleic acid construct" or "DNA construct" refers to an artificially constructed (i.e., not naturally occurring) DNA molecule that is capable of expressing the polypeptide. Nucleic acid constructs may be part of a vector that is used, for example, to transform a cell.

In another aspect, the present invention provides vectors comprising the constructs described herein. The term "vector" refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors". Vectors suitable for use with the present invention comprise the constructs described herein and heterogeneous sequence necessary for proper propagation of the vector and expression of the encoded polypeptide.

Preferably, the constructs are packaged in a vector suitable for delivery into a mammalian cell including but not limited to, an adeno-associated viral (AAV) vector, a lentiviral vector, or a vector suitable for transient transfection. As used herein, the term "vector," "virus vector," "delivery vector" (and similar terms) generally refers to a virus particle that functions as a nucleic acid delivery vehicle, and which comprises the viral nucleic acid (i.e., the vector genome) packaged within the virion. Suitable vectors are known and commercially available in the art. For example, see Deverman et al. (Cre-dependent selection yields AAV variants for widespread gene transfer to the adult brain, *Nature Biotechnology*, 34 (2): 204-209, 2016) and Chan et al. (Engineered AAVs for efficient noninvasive gene delivery to the central and peripheral nervous system, *Nature Neuroscience*, 20 (8): 1172-1179, 2017), which are incorporated herein by reference in their entirety. A skilled artisan will be familiar with the elements and configurations necessary for vector construction to encode the constructs described herein.

In some cases, a nucleic acid encoding one or more Ca$_v$3.2 inhibitory peptide aptamers is incorporated in a delivery vector (e.g., an AAV vector). For example, nucleic acids of this disclosure can be packaged in an AAV particle, an adenovirus particle, a herpesvirus particle, a baculovirus particle, or any other suitable virus particle. In some cases, a nucleic acid encoding one or more Ca$_v$3.2 inhibitory peptide aptamers can be operably associated with a promoter element.

The constructs provided herein may include a promoter operably linked to any one of the polynucleotides described herein. As used herein, a polynucleotide is "operably connected" or "operably linked" when it is placed into a functional relationship with a second polynucleotide sequence.

As used herein, the terms "heterologous promoter," "promoter," "promoter region," or "promoter sequence" refer generally to transcriptional regulatory regions of a gene, which may be found at the 5' or 3' side of a polynucleotides described herein, or within the coding region of said polynucleotides. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

Heterologous promoters useful in the practice of the present invention include, but are not limited to, constitutive, inducible, temporally-regulated, developmentally regulated, chemically regulated, tissue-preferred and tissue-specific promoters. The heterologous promoter may be a plant, animal, bacterial, fungal, or synthetic promoter. Suitable promoters are known and described in the art. In some embodiments, a suitable promoter is the chimeric CMV-chicken β-actin (CBA) promoter.

In some cases, the construct is an adeno-associated virus (AAV) vector comprising a heterologous nucleic acid sequence operably linked to regulatory sequences which direct expression of a product from the heterologous nucleic acid sequence in a host cell, where the expression product of the heterologous nucleic acid sequence comprises one or more Cav3.2 inhibitory peptide aptamers. The expression product of the heterologous nucleic acid sequence can comprise the peptide set forth as SEQ ID NO: 1 or another sequence or portion thereof presented in Table 1. In some cases, vector is selected from AAV type 1, AAV type 2, AAV type 3 (including types 3A and 3B), AAV type 4, AAV type 5, AAV type 6, AAV type 7, AAV type 8, AAV type 9, AAV type 10, AAV type 11, among others.

In some cases, the AAV vector construct is combined with a pharmaceutically acceptable carrier to form a pharmaceutical composition. Preferably, the pharmaceutically acceptable carrier is a liquid suitable for administering the construct by injection. As used herein, the term "carrier" refers to a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, may be found in the U.S. Pharmacopcia National Formulary, 1857-1859, (1990).

Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator.

Examples of pharmaceutically acceptable antioxidants include water soluble antioxidants such as ascorbic acid, cysteine hydrochloride, sodium bisulfite, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like.

In another embodiment, the present formulation may also comprise other suitable agents such as a stabilizing delivery vehicle, carrier, support or complex-forming species. The coordinate administration methods and combinatorial formulations of the instant invention may optionally incorporate effective carriers, processing agents, or delivery vehicles, to provide improved formulations for delivery of the Cav3.2 inhibitory peptide aptamer described herein.

The formulation may additionally include a biologically acceptable buffer to maintain a pH close to neutral (7.0-7.3). Such buffers preferably used are typically phosphates, carboxylates, and bicarbonates. More preferred buffering agents are sodium phosphate, potassium phosphate, sodium citrate, calcium lactate, sodium succinate, sodium glutamate, sodium bicarbonate, and potassium bicarbonate. The buffer may comprise about 0.0001-5% (w/v) of the vaccine formulation, more preferably about 0.001-1% (w/v). Other excipients, if desired, may be included as part of the final vaccine formulation.

The term "sequence identity" as used herein refers to the extent that sequences are identical on a nucleotide-by-nucleotide basis or an amino acid-by-amino acid basis over a window of comparison. Nucleic acid and protein sequence identities can be evaluated by using any method known in the art. For example, the identities can be evaluated by using the Basic Local Alignment Search Tool ("BLAST"). The BLAST programs identity homologous sequences by identifying similar segments between a query amino or nucleic acid sequence and a test sequence which is preferably obtained from protein or nuclei acid sequence database. The BLAST program can be used with the default parameters or with modified parameters provided by the user.

The term "percentage of sequence identity" is calculated by comparing two optimally aligned sequences over the window of comparison, determining the number of positions at which the identical nucleic acid base (e.g., A, T, C, G) or the identical amino acid residue (e.g., Ala, Pro, Ser, Thr, Gly, Val, Leu, lie, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Methods

In another aspect, provided herein are methods for treating pain in a subject. In some cases, a method for treating pain in a subject comprises administering to the subject the inhibitory polypeptides, constructs, vectors or compositions described herein. In some cases, the inhibitory polypeptides, constructs, vectors or compositions described herein may be formulated with a pharmaceutically acceptable carrier for administration to a patient in need thereof.

To function as therapeutic agents, the constructs described herein are delivered into neurons or ganglia thereof of a subject in need of treatment. Preferably, the method comprises targeted delivery of the constructs comprising a nucleic acid encoding one or more $Ca_v3.2$ inhibitory peptide aptamers. Targeted injection limits systemic exposure upon administration to the subject. For example, targeted delivery can comprise injecting a nucleic acid encoding one or more $Ca_v3.2$ inhibitory peptide aptamers into or nearby neural tissue of the subject. Examples of neural tissues into which a composition described herein can be injected include, without limitation, ganglia (e.g., the dorsal root ganglia), spinal nerve, preganglionic fibers, and paraganglia. Examples of neural tissues nearby which a composition described herein can be injected include, without limitation, the periganglionic subarachnoid space. In preferred embodiments, administering comprises injecting a composition comprising a nucleic acid encoding one or more $Ca_v3.2$ inhibitory peptide aptamers into a dorsal root ganglion. Expression of the $Ca_v3.2$ inhibitory peptide aptamer in the DRG inhibits nociceptive DRG neuron excitation and, thus, treats pain in the subject receiving the injection.

A $Ca_v3.2$ inhibitory peptide aptamer described herein can be administered using any appropriate delivery vehicle. For example, in some cases, a nucleic acid encoding an inhibitory peptide aptamer useful for treating pain, the nucleic acid can be incorporated into a delivery vehicle that can drive expression of the nucleic acid. Examples of delivery vehicles include, without limitation, non-viral vectors (e.g., plasmids (e.g., expression plasmids), liposomes, and polymersomes) and viral vectors (e.g., adeno-associated virus vectors, HSV vectors, and lentiviral vectors). For example, a nucleic acid encoding one or more $Ca_v3.2$ inhibitory peptide aptamers useful for treating pain can be delivered using an adeno-associated virus (AAV) vector. As used herein, the term "adeno-associated virus" (AAV) includes, without limitation, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. Sec, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004) J. Virol. 78:6381-6388), which are also encompassed by the term "AAV." The genomic sequences of various AAV and autonomous parvoviruses, as well as the sequences of the ITRs, Rep proteins, and capsid subunits are known in the art. Such sequences may be found in the literature or in public databases such as the GenBank database.

In some cases, the vector for delivery is an AAV vector produced by modified capsids, which have been shown to improve gene transfer efficiency with potentially reduced immunogenicity compared with naturally occurring serotypes. Sec, e.g., Buning & Srivastava, *Mol Ther Methods Clin Dev* 12:248-265, (2019). For example, Anc80L65 (anc80), which is a novel AAV capsid designed from in silico reconstruction of the viral evolutionary lineage, has been demonstrated robust transduction capabilities after local delivery in various tissues. See Wang et al., *PLOS One* 12:00182473, (2017); Hudry et al., *Mol Ther Methods Clin Dev* 10:197-209, (2018).

As used herein, the term "treating" refers to improving, reducing, eliminating, or lessening the severity of any aspect of pain in a subject. For purposes of this invention, treating pain includes, without limitation, alleviating one or more clinical indications of pain and reducing the severity of one or more clinical indications of pain. For example, the pain can be neuropathic pain or chronic pain. Typically, aspects of pain are assessed using subjective self-report measures. For example, pain assessment can include obtaining a subject's self-report of pain using, in some cases, a pain intensity scale such as the Verbal Rating Scale (VRS), the Visual Analogue Scale (VAS), or the Numerical Rating Scale (NRS). Pain can be assessed prior to, during, or post-administration of an effective amount of a $Ca_v3.2$ inhibitory peptide aptamer as described herein.

In another aspect, the disclosure provides a method of inhibits $Ca_v3.2$ T-type calcium channel activity in the dorsal root ganglion (DRG) in a subject in need thereof, the method comprising administering to the dorsal root ganglion a therapeutically effective amount of the inhibitory polypeptide, construct, vector, adeno-associated virus (AAV) described herein capable of expressing the inhibitory peptide, or pharmaceutical composition described herein, wherein $Ca_v3.2$ T-type calcium channel activity is inhibited. In some embodiments, the administration is local administration, for example, injecting a therapeutically effective amount of AAV particles encoding the inhibitor peptide into a dorsal root ganglion of the subject, whereby the inhibitory peptide is expressed and inhibits $Ca_v3.2$ T-type calcium channel activity. In some apsects, the administering step results in reducing nociceptive dorsal root ganglion (DRG) neuron excitation. In some aspects, the subject in need has pain, chronic pain, or neuropathic pain.

As used herein, the terms "subject" and "patient" are used interchangeably and can encompass a human or animal including, without limitation, a dog, cat, horse, cow, pig, sheep, goat, chicken, rodent, e.g., rats and mice, and non-human primate, e.g., monkey. Preferred subjects are human subjects. The human subject may be a pediatric, adult or a geriatric subject. As used herein, the phrase "in need thereof" indicates the state of the subject, wherein therapeutic or preventative measures are desirable. Appropriate subjects for the methods described herein include, without limitation, humans diagnosed as having or suspected of having a pain condition (e.g., neuropathic pain, chronic pain, regional pain). In some cases, methods for treating pain in a subject (e.g., a human) can include identifying the subject as having pain or as being at risk of developing pain. Any appropriate method can be used to identify a mammal having pain or at risk for developing pain. In some cases, a subject having pain or at risk of developing pain can be diagnosed by a medical professional (e.g., a medical professional experienced in the diagnosis of pain syndromes and/or disorders of the peripheral nervous system such as anesthesiologists, neurologists, orthopedists, neurosurgeons, physiatrists, radiologists, and interventional radiologists). In some aspects, the pain is chronic pain, and in further aspects the pain is neuropathic pain.

In some embodiments, the method comprises administering a therapeutically effective amount of constructs comprising a nucleic acid encoding one or more $Ca_v3.2$ inhibitory peptide aptamers. As used herein, the terms "effective amount" or "therapeutically effective amount" refer to a sufficient amount of a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for a method provided herein can be the amount of a compound described herein (e.g., a $Ca_v3.2$ inhibitory peptide aptamer) that is required to provide a clinically significant decrease in any aspect of neuropathic pain or chronic pain. An effective amount can vary depending on, inter alia, the $Ca_v3.2$ inhibitory peptide aptamer used, the type of pain and its severity, and the age, weight, etc., of the subject to be treated. An appropriate effective amount in any individual case may be determined using techniques known to those in the art, such as a dose escalation study. Effective amounts of therapeutic agents can depend on other various factors, such as the frequency of administration, the duration of treatment, the severity of the condition being treated, the condition and prior medical history of the subject being treated, the possibility of co-administration with other therapeutic treatments such as use of other agents, and the judgment of the treating physician. A dose that is lower than an effective dose can initially be administered to a subject, and the dose can then be gradually increased over time until the desired effect is achieved.

In cases in which the constructs are delivered as a viral vector (e.g., an AAV vector), expression of the encoded peptide(s) is achieved by transduction of the viral vector into the injected tissue (e.g., DRG). As used herein, "transduction" of a cell by a virus vector (e.g., an AAV vector) means entry of the vector into the cell and transfer of genetic material into the cell by the incorporation of nucleic acid into the virus vector and subsequent transfer into the cell via the virus vector. Generally, when delivering a vector comprising a construct of this disclosure by transfection, the vector is delivered in an amount from about 5 μg to about 100 μg DNA, about 10 μg to about 50 μg DNA to about $1 \times 10^4$ cells to about $1 \times 10^{13}$ cells, or about $1 \times 10^5$ cells. However, the relative amounts of vector DNA to host cells may be adjusted by one of ordinary skill in the art, who may take into consideration such factors as the selected vector, the delivery method and the host cells selected.

The frequency and duration of administration can be any frequency or duration that improves a symptom of, for example, chronic pain without being toxic. For example, an agent can be administered once or twice a day, once every other day, once or twice a week, or as needed. The frequency of administration can remain constant or can be variable during the duration of treatment. An effective duration of treatment can vary from several weeks to several months or years. For example, an effective duration of treatment can be six months, five years, or a lifetime. In addition, a course of treatment can include rest periods. Multiple factors can influence the actual effective frequency and duration of treatment. For example, the activities of the particular therapeutic agents used, the severity of the condition being treated, the doses administered, and the condition and prior medical history of the mammal being treated can affect the effective frequency and duration of treatment.

The administering step is preferably targeted to specific cells, e.g., dorsal root ganglion cells, in order to provide the necessary therapeutic effect and to reduce off-target side effects. In some embodiments, the administering is performed by local injection. In other embodiments, the administering is targeted by using a targeting molecule specific to the cell type, e.g., dorsal root ganglion.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the compositions can mean plus or minus a range of up to 20%, preferably up to 10%, more preferably up to 5%.

The present invention has been described in terms of one or more preferred embodiments, and it should be appreciated that many equivalents, alternatives, variations, and modifications, aside from those expressly stated, are possible and within the scope of the invention.

EXAMPLES

Example 1: Targeting Intrinsically Disordered Regions Facilitates Discovery of T-Type/Cav3.2 Inhibitory Peptides for AAV-Mediated Analgesia Development of sensory neuron-specific inhibitors of $Ca_v3.2$ channels is an opportunity for achieving analgesic therapeutics, but success has been elusive. Small peptides, especially those derived from the natural proteins as functionally interfering peptide aptamers (iPAs), can produce highly effective and selective blockade of specific nociceptive molecular pathways to reduce pain with minimal off-target effects.

In this Example, we report the engineering of potent and selective iPAs of the T-type/$Ca_v3.2$ from the intrinsically disordered regions (IDRs) of Cav3.2 intracellular segments. We localized IDR domains in Cav3.2 protein and identified a number of $Ca_v3.2$iPA candidates that significantly reduce Cav3.2 current in HEK293 cells stably expressing human wide-type $Ca_v3.2$. Adeno-associated viral vector (AAV)-mediated expression of a prototypic $Ca_v3.2$iPA1, derived from the IDRs of $Ca_v3.2$ intracellular loop 2, selectively in dorsal root ganglia sensory neurons in vivo produces sustained inhibition of calcium current conducted by T-type channels in PSNs and pain attenuation in a tibial nerve-injury (TNI) neuropathic pain rat model, demonstrating its therapeutic potential for pain treatment. Our results indicate that the $Ca_v3.2$iPAs are promising analgesic leads that, combined with AAV-targeted gene delivery in anatomically segmental sensory ganglia, have the potential for future clinical development as novel therapeutics in the treatment of pain.

$Ca_v3.2$ protein consists of four highly structured homologous transmembrane domains (I-IV), connected by intracellular loops and flanked by intracellular N- and C-termini that serve as essential molecular interfaces for $Ca_v3.2$ regulatory signaling networks. Fully understanding of functional domains in $Ca_v3.2$ IDRs is currently limited, but would be valuable in understanding of $Ca_v3.2$ regulation and for future drug development. Here, we identified highly disordered regions in $Ca_v3.2$ protein, and defined a number of $Ca_v3.2$iPAs that significantly reduce $Ca_v3.2$ current. AAV-mediated expression of a prototype $Ca_v3.2$iPA1 in DRG neurons in vivo produces sustained T-current inhibition in PSNs and pain attenuation in a TNI neuropathic pain rat model, suggesting a potential analgesic lead for pain treatment.

Results

In Silico Prediction of Cav3.2-IDRs and Design of Candidate Cav3.2 Interfering Peptide Aptamers ($Ca_v3.2$iPAs)

We used the full amino acid (aa) sequence of rat voltage-dependent T-type calcium channel subunit alpha-1H ($Ca_v3.2$, UniProtKB-Q9EQ60), which has ~95% homology with human $Ca_v3.2$ (UniProtKB-095180). To identify specific IDRs, we analyzed the full-length rat $Ca_v3.2$ sequence using DEPICTER (DisorderEd Prediction CenTER) that combines 10 popular algorithms for IDRs and IDR function predictions upon primary sequence, based on amino-acid (aa) biophysical features for the protein's disordered ensemble. Prediction returns a score between 0 and 1 for each residue, indicating the degree of given residue being part of an ordered or disordered region (residues with scores >0.5 are considered as disordered). Results revealed clear order-to-disorder transitions where $Ca_v3.2$ transmembrane (TM) domains and intracellular portions join, and scores indicate a definitely disordered nature of $Ca_v3.2$ intracellular regions (FIG. 1A, B). Specifically, the most extensive predicted IDRs are located in the intracellular loops and termini, while protein TM domains are highly ordered. DEPICTER also includes three accurate consensus predictors of disorder and disordered protein binding, as well as DNA/RNA bindings.

Due to their extended conformation, IDRs are more exposed to other proteins and are preferred post-translational modification (PTM) sites, including sites for methylation, ubiquitination, and especially for phosphorylation, which are not only most prevalent but also serve as critical signaling nodes. Potential phosphorylation sites in $Ca_v3.2$ full-length aa sequence were identified using Disorder Enhanced Phosphorylation Predictor (DEPP) and high-throughput profiles that phosphorylation sites are assigned by proteomic discovery mass spectrometry (PhosphoSitePlus v6.5.8). Results showed that the majority of potential phosphorylation residues (serine, threonine, and tyrosine with high DEPP scores) reside in $Ca_v3.2$ IDRs, and particularly in the IDRs within intracellular loop (ICL) 1, ICL2, and C-terminus (FIG. 1C). $Ca_v3.2$ IDRs feature as potential PPI binding sites and short linear peptides can be the key binding motifs and domains of $Ca_v3.2$ regulatory signaling interactome.

These observations predict that the focusing on the $Ca_v3.2$ IDRs is a valuable approach for the search for short peptides effective in $Ca_v3.2$ functional regulation. A comparison of the components of $Ca_v3.2$-IDRs to the IDRs in a number of known nociception-related ion channels (FIG. 1D) showed that $Ca_v3.2$ is particularly enriched with IDRs which can be acted upon by a diverse array of regulatory peptides.

The potentially functional domains within the $Ca_v3.2$ IDRs (ie. short linear peptides defined as functional IDD) were analyzed using "Motifs", "Eukaryotic Linear Motif" (ELM), and SLIMPrep. The SLIMPrep predicts short linear motifs (SLiMs) based on strongly conserved SLIMs which relies on the primary amino acid sequence of the protein, and SLIMPrints, followed by filtering based on the prediction scores. The enumerated motifs suggest many possible functional peptides that could potentially associate with various predicted $Ca_v3.2$IDR peptides as 'hot-spot' functional IDDs, including proteolytic cleavage sites, ligand binding sites, PTM sites, and sub-cellular targeting sites. Notably, $Ca_v3.2$ IDRs contain a number of linear polybasic peptide (PBP) sequences composed of ~10-22 aa, enriched with positively charged arginine (R) and lysine (K), clustered in ICL1-3 and C-terminus, enriched with other disordered aa and phosphorylation sites, and potentially as the protein regulating sites, since several studies report that polybasic sequences in protein IDRs are crucial in the functional regulation of proteins and positively charged polybasic domains can be essential for recruiting multiple signaling proteins. These PBP peptides and a 20mer peptide from the N-terminal IDR of $Ca_v3.2$ ($Ca_v3.2$NP) were designed computationally or supplemented by a reading of the literature, and are the focus as $Ca_v3.2$iPA candidates (FIG. 1E). Notably, candidate $Ca_v3.2$iPA3 sequence locates within the proximal peptide of $Ca_v3.2$-ICL1 that regulates $Ca_v3.2$ gating and the $Ca_v3.2$iPA2 sequence is largely overlaid to a peptide in $Ca_v3.2$-ICL3 that interacts with nuclear expressed deubiquitinating enzyme USP5.

Expression of $Ca_v3.2$iPAs

To allow functional engagement of $Ca_v3.2$ channels by candidate $Ca_v3.2$iPAs, we first constructed AAV shuttle plasmids containing transgene expression cassettes encoding various GFP-$Ca_v3.2$iPA chimeras, with which we expressed GFP-$Ca_v3.2$iPAs (3.2iPAs) for transfection. Specifically, the sequences for interchangeable peptide for testing were cloned with a linker sequence (GLRSRAQASN-SAVDGTAGPGS, SEQ ID NO: 6) derived from plasmid pEGFP1 (Clontech, San Francisco, CA), to form a chimeric transgene in a GFP-linker-3.2iPA orientation driven by a chimeric CMV-chicken β-actin (CBA) promoter to generate pAAV-CBA-GFP-3.2iPA (pAAV-3.2iPA) expression plasmids, in which the oligonucleotide encoding the interchangeable iPAs are inserted at the 3' end of GFP (FIG. 1F). The crystal structure analysis of designed GFP3.2iPA1 by I-TASSER tool showed an unfolded and extended, highly flexible structural ensemble of linker-3.2iPA1, which is compatible with a well-exposed mode to bind to targets (FIG. 1H, other iPAs not shown). Stable expression of each construct was verified by transfection into HEK293 cells (FIG. 1G, I).

Inhibition of Cav3.2 Current ($I_{Ca3.2}$) by Cav3.2iPAs

Figure 2:
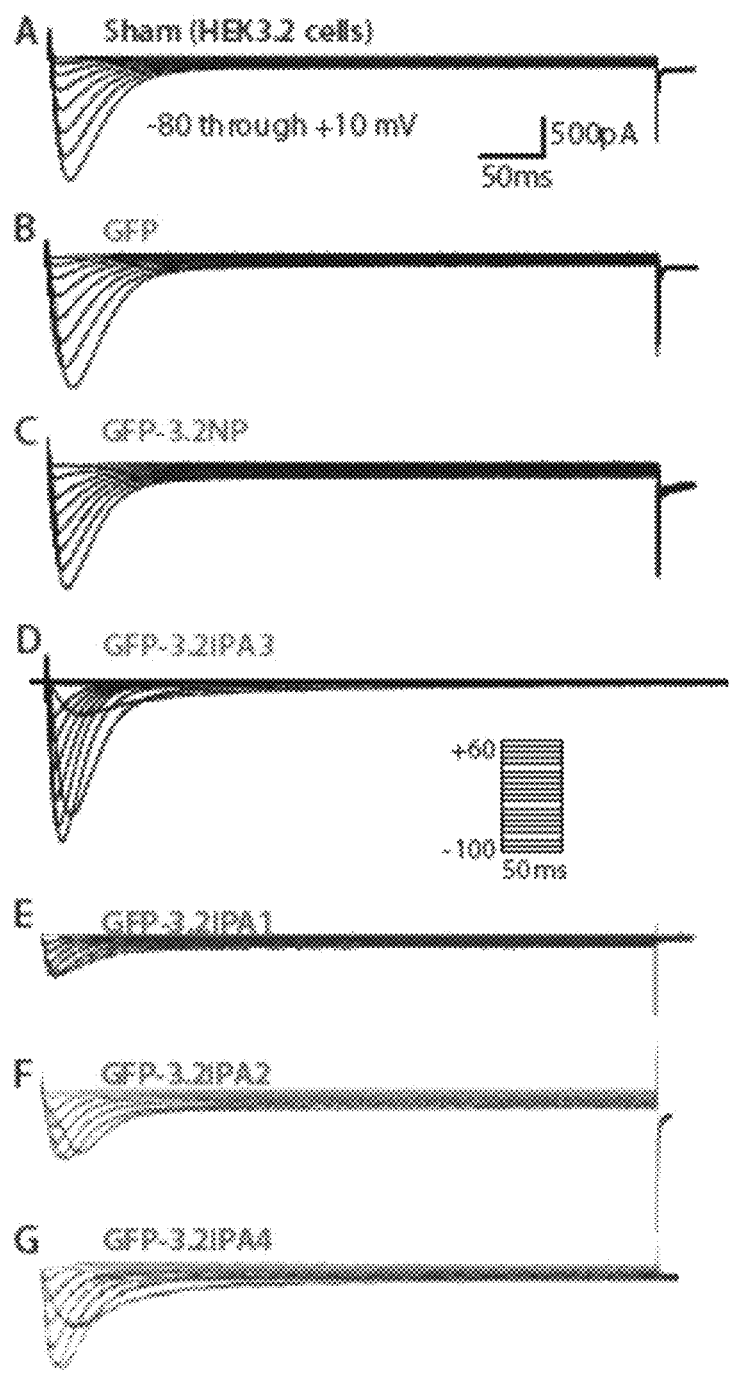
FIG. 2. Inhibition of $Ca_v3.2$ current ($I_{Ca3.2}$) by $Ca_v3.2$iPA candidates (HEK3.2 cells). Shown are results of functional testing of potential Cav3.2iPAs in block of $I_{Ca3.2}$ in HEK293 cells stable expression of human Cav3.2 ('HEK3.2'). Representative $Ba^{2+}$ current traces elicited by whole-cell patch-clamp recording for sham-transfected HEK3.2 cells (A), or transfected with plasmids coding GFP (B), GFP3.2NP (C), GFP3.2iPA3 (D), GFP3.2iPA1 (E), GFP3.2iPA2 (F), and GFP3.2iPA4 (G), respectively, in response to 400 ms depolarizing steps ranging between −90 mV and 60 mV in 10 mV increments from a holding potential of −100 mV (insets: recording protocol and current/time scales). Comparison of corresponding mean peak current density-voltage (I/V) relationship from different constructs as indicated (H) and quantitative analysis of averaged peak $I_{Ca3.2}$ density (I); *$p<0.05$ and ***$p<0.001$, one-way ANOVA followed by Tukey post hoc multiple comparisons. No effects of expression of GFP3.2iPA1 and GFP3.2iPA2 were observed on steady-state activation (J, inset: V50 activation) and inactivation (K, inset: V50 inactivation), compared to sham- and GFPNP-transfected cells.
Figure 2:
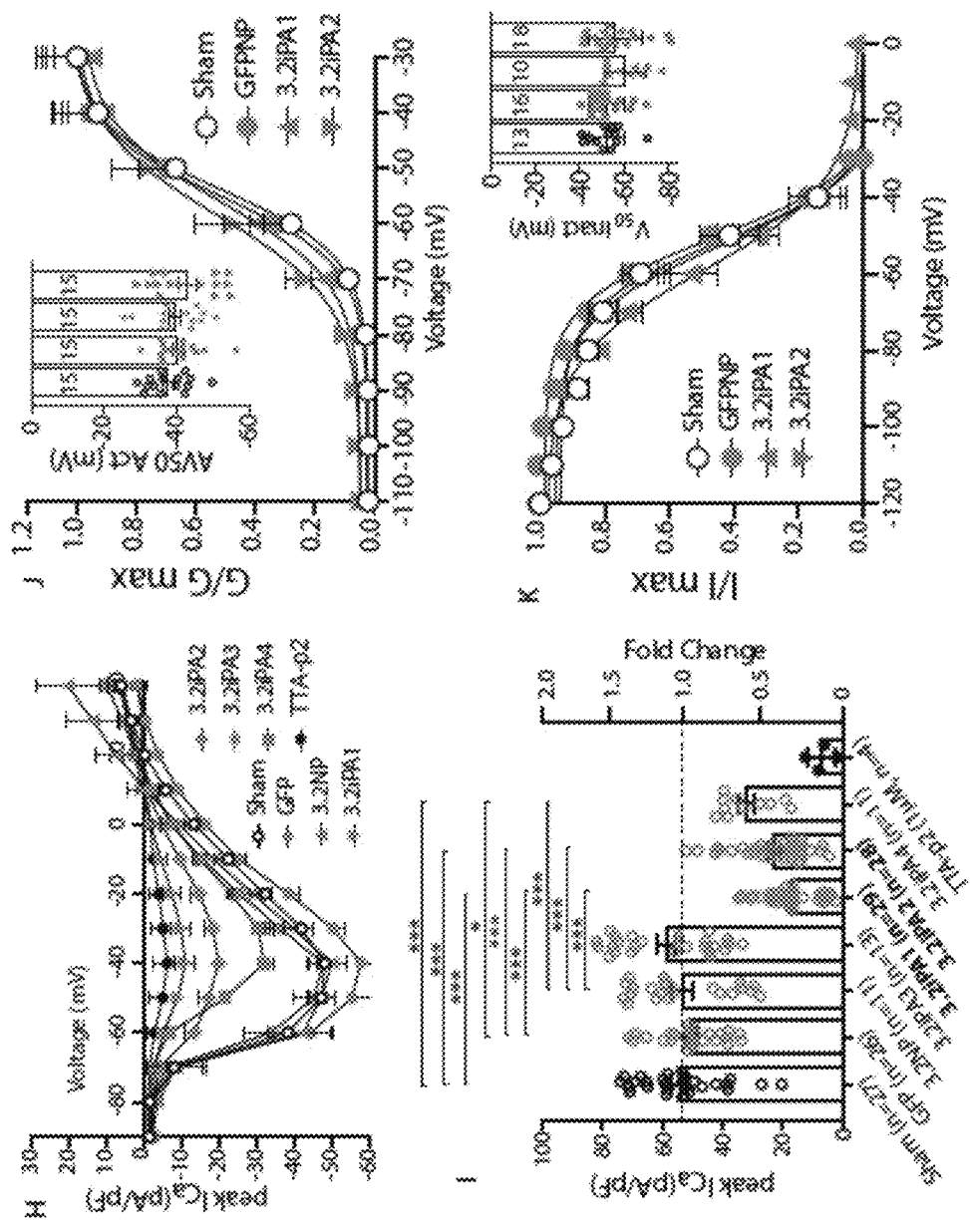
Figure 3:
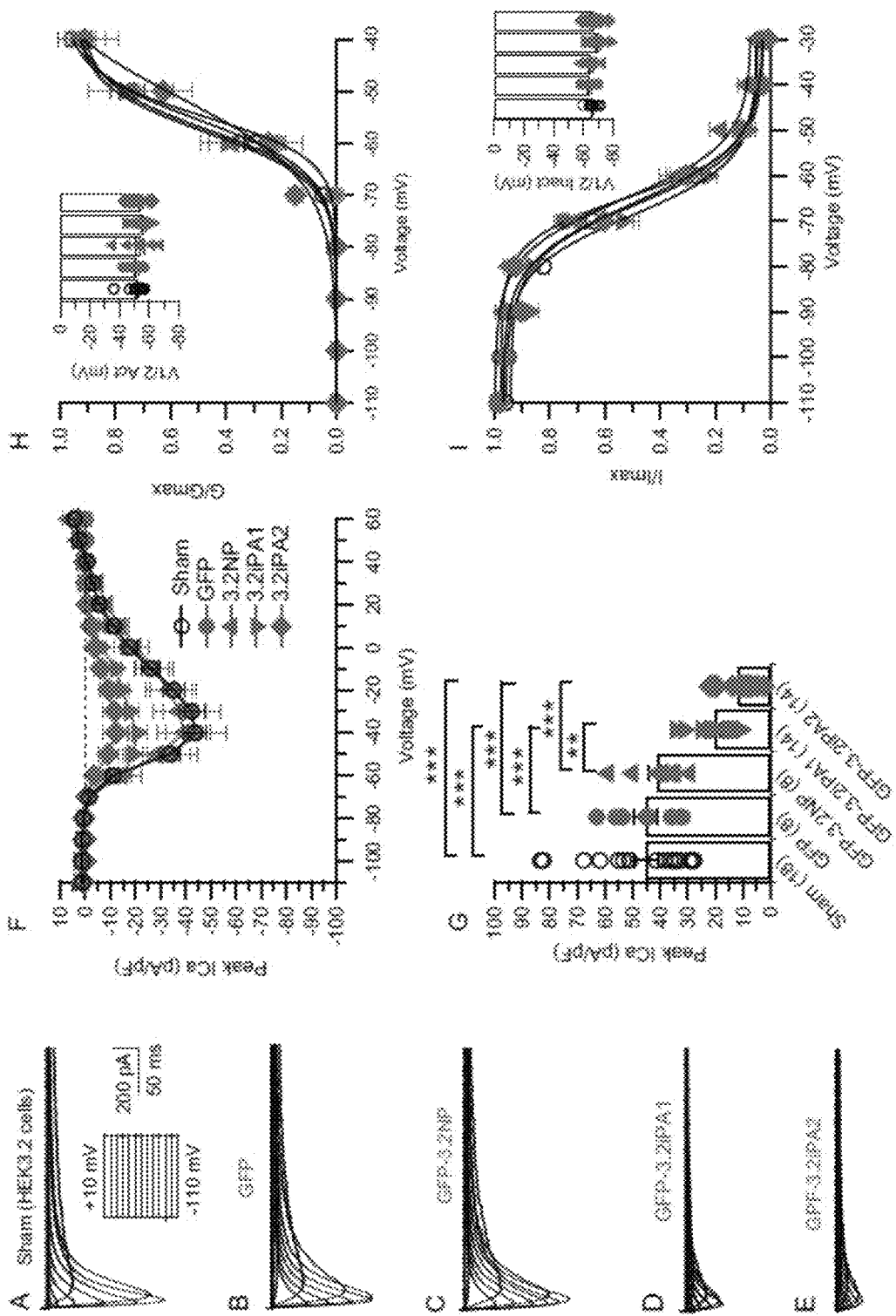
FIG. 3. Stony Brook University: Inhibition of Cav3.2 current ($I_{Ca3.2}$) by Cav3.2iPA candidates (HEK3.2 cells).

Whole-cell voltage-clamp recordings in HEK293 cells stably expressing human wide-type $Ca_v3.2$ (HEK3.2) transfected with plasmids encoding different GFP3.2iPAs were performed to characterize functional engagement of $Ca_v3.2$ channels by designed $Ca_v3.2$iPAs (3.2iPAs). Application of the T-type calcium channel blocker TTA-P2 reduced peak $Ca_v3.2$ current density ($I_{Ca3.2}$) to ~5% of baseline (FIG. 2), consistent with T-type calcium current. Transfection results showed that 3.2iPA1, 3.2iPA2, and 3.2iPA4 produced ~70%, ~60%, and 40% reduction of peak $Ca_v3.2$ current density ($I_{Ca3.2}$), respectively, while transfection with plasmids expressing the GFPlinker, 3.2NP, and 3.2iPA3 showed no significant effect on peak $I_{Ca3.2}$ density compared to sham-transfected cells. These experiments thus identified GFP3.2iPA1 and GFP3.2iPA2 as the effective iPAs (>50% $I_{Ca3.2}$ inhibition). Additionally, their effects on $Ca_v3.2$ biophysical properties were examined by using sham- and GFP3.2NP (3.2NP) as the controls. Results revealed no significant shifts of the steady-state activation and inactivation curves, nor on voltage-activated half activation or half inactivation (FIG. 2), suggesting that 3.2iPA1 and 3.2iPA2 reduced the conduction of $Ca^{2+}$ through $Ca_v3.2$ channels but did not change channel activation and inactivation properties. To test the replicability of these findings, the experiments testing the effects of 3.2iPA1 and 3.2iPA2 expression on $I_{Ca3.2}$ in HEK3.2 cells were examined independently by a separate research team at a different institution, and results were similar (FIG. 3). Taken together, these findings confirm the efficacy of our discovery approach and indicate that signaling through PBP sequences in $Ca_v3.2$ IDRs is important in $Ca_v3.2$ channel function. The findings also suggest that 3.2iPA1 and 3.2iPA2 successfully engage $Ca_v3.2$, thereby justifying further studies of their potential as therapeutic agents. Potent $Ca_v3.2$ current inhibition by 3.2iPA1 was confirmed in neuronal NG108-15 cells that naturally express $Ca_v3.2$. In this cell line, we also found expression of $Ca_v3.2$ in subcellular locations (FIG. 8).

No Effects of $Ca_v3.2$iPAs on Sodium Channel 1.7 (Nav1.7) and Voltage-Gated Potassium Channels (VGKCs)

T-type calcium channel specificity of $Ca_v3.2$iPAs action was further examined by using NG108-15 cells that naturally express Nav1.7 and voltage-gated potassium channels (VGKCs). Whole-cell patch-clamp recordings showed that transfection of 3.2iPA1 and 3.2iPA2 have no significant effects on the Nav1.7 current (INa1.7) and the VGKC current (IKv), as compared to NG108-15 sham-transfected cells or NG108-15 cells transfected with plasmids encoding GFP or GFPNP (FIG. 9, 10).

Inhibition of LVA but not HVA Calcium Channels by $Ca_v3.2$iPA1 and $Ca_v3.2$iPA2 in Rat PSNs Because no heterologous system or cell lines can fully mimic in vivo conditions of sensory neurons, we further tested the functional engagement of calcium channels by $Ca_v3.2$iPAs in vivo. AAV6 vectors encoding GFPNP, GFP3.2iPA1, GFP3.2iPA2, and GFP3.2iPA3 were injected into lumbar (L) 4/5 DRG of naïve rats, and acutely dissociated sensory neurons from DRG were tested at 4 wk post-injection. Patch-clamp recordings from small/medium-sized PSNs showed that AAV-mediated expression of 3.2iPA1 and 3.2iPA2 produced significant inhibition of peak LVA $I_{Ca}$ (pA/pF) by ~70% and ~60%, respectively, while 3.2iPA3 enhanced peak LVA $I_{Ca}$ by ~30%, compared to control cells. No change of peak LVA $I_{Ca}$ was observed in PSNs expressing GFPNP compared to control cells (FIG. 4A-G). To further test effects of the iPA1 on $Ca^{2+}$ influx through PSN $Ca_v3.2$ channels, $Ca^{2+}$ microfluorimetry was performed in dissociated PSNs. PSNs were depolarized by exposure to 50 mM $K^+$ for 0.3 s, in the presence of Tetrodotoxin (IpM) to eliminate action potential generation as previously described. Results showed that AAV-mediated 3.2iPA1 expression in PSNs significantly depressed $Ca^{2+}$ influx under these conditions (FIG. 4H, I). Patch-clamp recordings showed no effect of GFP3.2iPA1 and GFP3.2iPA2 on peak HVA $I_{Ca}$ (FIG. 4J-Q). Importantly, AAV-encoded 3.2iPA1 expression in vivo did not significantly affect baseline mechanical (vF) and thermal (heat) thresholds in control rats (FIG. 6A, see below). Taken together, 3.2iPA1 expression in PSNs appears to be a potential lead for further testing as potential analgesics.

Attenuation of TNI-Induced Hypersensitivity by AAV6-Cav3.2iPA1 In Vivo

We next focused to test whether AAV-mediated $Ca_v3.2$iPA1 expression selectively in the PSNs could reduce hypersensitivity to mechanical and thermal stimuli following peripheral nerve injury. AAVs, expressing GFP-3.2iPA1 and GFPNP as the control, were packaged into serotype 6 since this serotype efficiently transduces nociceptive PSNs, which express $Ca_v3.2$. The specificity of $Ca_v3.2$ antibody used to detect $Ca_v3.2$ expression was validated by immunoblots upon cell lysates of stable cell lines expressing different calcium channels, showing the antibody recognizing $Ca_v3.2$ but no other T-type channel isoforms nor $Ca_v2.2$ (FIG. 5A). Immunoblots on DRG samples from naïve rats revealed that $Ca_v3.2$ protein was more enriched in the cytosolic and nuclear fractions than in the plasma membrane (FIG. 5B).

AAV-mediated 3.2iPA1 expression in DRG-PSNs on pain behavior was evaluated by using the TNI neuropathic pain model in adult male rats. Stimuli were applied to the lateral margin of the plantar aspect of the paw in the sural area of innervation, as we described previously. Specifically, after behavior tests for baseline stabilized sensitivity to mechanical and thermal cutaneous stimulation, rats were randomized to receive intraganglionic vector injection of either AAV6-3.2iPA1 or AAV6-GFPNP, into both the ipsilateral L4 and L5 DRG immediately after TNI surgery. Subsequent sensory behavior evaluation was performed on a weekly basis for an additional 5 weeks, after which tissues were harvested for IHC characterization of transgene and target gene expression, and for current-clamp recordings of PSN neuronal activity (see below). The in vivo transduction rate for AAV6-$Ca_v3.2$iPA1 5 weeks after TNI and vector injection was determined by IHC as previously reported. GFP3.2iPA1-positive neurons comprised 48±5% (971 out of 1898 total neuronal profiles, positive for pan-neuronal marker β3-tubulin, n=3 DRG, five sections per DRG, which were selected as every fifth section from the consecutive serial sections). Transduced DRG neurons included the full size range of the PSNs that also expressed $Ca_v3.2$ and GFP3.2iPA1 with multiple subcellular localization. GFP3.2iPA1-IR signals were detected in spinal dorsal horn neuropils, sciatic nerve, and hindpaw afferent terminals (FIG. 5C-5H). Behavioral evaluations showed that all rats established significant pain behaviors after TNI, which included lowered withdraw threshold from mild mechanical stimuli (vF testing), more frequent hyperalgesic-type responses (sustained lifting, shaking, grooming) after noxious mechanical stimulation (Pin testing), reduced withdraw threshold to heat and more frequent withdrawals from cold (Acetone stimulation). These behaviors persisted after injection of the control vector (AAV6-GFPNP) during the 5 weeks of observation course. In contrast, TNI rats injected with AAV6-3.2iPA1 showed gradual reversal of these changes starting about 2 weeks after treatment (FIG. 6B-6F). These findings suggest that AAV6-mediated, DRG-targeted $Ca_v3.2$iPA1 expression has analgesic efficacy in reducing peripheral hypersensitivity in a rat model of neuropathic pain.

Reversal of TNI-induced PSN hyperexcitability by AAV6-Ca$_v$3.2iPAs treatment

We next determined whether AAV6-3.2iPA1 treatment reverses the enhanced neuronal excitability of nociceptive PSNs following TNI, using whole-cell current-clamp recording of DRG dissociated neurons. Although TNI produces DRG with co-mingled injured and uninjured axons, nerve-injury can induce an increase of voltage-gated ion channel activity in both axotomized neuron and adjacent intact neurons, as has long been recognized that some molecules related to nociception are upregulated in the intact L4 DRG neurons after L5 SNL, leading to similar electrophysiological changes and increased discharge frequency in axotomized and neighboring intact DRG neurons. We therefore recorded from randomly chosen small- and medium-sized neurons in cultures from dissociated L4 and L5 DRG. Sensory neurons (small/medium, <40 µm in diameter) dissociated from DRG of sham-operated rats and TNI rats without treatment, GFP-expressing neurons injected with AAV6-GFPNP and AAV6-3.2iPA1, were used for recording. The effect of AAV6-3.2iPA1 treatment on the repetitive firing properties of DRG neurons was assessed by applying a series of 250-ms current injections to the DRG dissociated neurons. Results showed that the frequency of APs evoked by progressively greater depolarizations in the recorded neurons from TNI rats were significantly increased, compared to sham controls. The increased PSN excitability in TNI rats was normalized in the transduced neurons after AAV6-3.2iPA1 treatment, whereas GFPNP-transduced neurons had no effect (FIG. 7). Together, these findings indicate that reversal of nerve injury-induced sensory neuron hyperexcitability by 3.2iPA1 may contribute to its attenuation of neuropathic pain behaviors.

Discussion

The Ca$_v$3.2 channels are an important class of targets for drugs that are critically needed for clinical treatment of chronic pain. Not only do Ca$_v$3.2 channelopathies underlie a critical mechanism for a variety of pain conditions, but modifying Ca$_v$3.2 function has proven to be a useful preclinical intervention in treatment of pain. In this study, a combined in silico/experimental strategy was used to design iPAs by targeting Ca$_v$3.2 IDRs. Promising candidates were selected and validated using in vitro and in vivo methods and AAV-mediated expression of a prototypic Ca$_v$3.2iPA1 produces sustained inhibition of calcium current conducted by T-type channels in PSNs and attenuates pain in the TNI rat model, demonstrating its therapeutic potential for pain treatment.

Progress has been made over the last decade to develop more selective and efficacious T-type/Ca$_v$3.2 blockers to treat pain. However, the clinically available small molecule Ca$_v$3.2 blockers used to treat pain applied systemically and orally are non-selective across different tissues and contribute to off-site effects. Thus, in spite of preclinical studies demonstrating that decreased T-type/Ca$_v$3.2 activity leads to a reduction in pain, few molecules targeting this gene product have reached the final phase of clinical trials, and many small molecules targeting T-type/Ca$_v$3.2 have failed to be validated as pain drugs. Most common pain conditions are triggered or maintained by PSN hypersensitivity originating at the site of the peripheral injury. Thus, development of novel peripheral acting strategies for T-type/Ca$_v$3.2 inhibition would be an ideal approach for clinical pain treatment.

Our approach used here includes a novel strategy in which highly selective and nontoxic T-type/Ca$_v$3.2iPAs are designed and developed from Ca$_v$3.2 IDRs, and these are delivered by using AAV in an anatomically targeted fashion that restricts block of T-type/Ca$_v$3.2 to the PNS. In preclinical models, direct DRG delivery of AAVs encoding analgesic biologics can provide relief in chronic pain, with high transduction efficiency, flexibility for selective segmental localization, and minimal behavioral changes attributable to the surgical procedure. Small peptides that mimic target protein sequences can serve as decoy molecules to selectively interfere with the function of their target signaling protein by preemptively binding to it. We have successfully employed this strategy in rat models to induce analgesia by preventing assembly of functional TRPV1 channels and by blocking membrane trafficking of Ca$_v$2.2 channels by interrupting its interactions with the structural protein CRMP-2. Here, we extended the applicability of DRG-AAV strategy to the analgesic effectiveness of PSN T-type/Ca$_v$3.2 blockade for neuropathic pain. Because activation of T-type/Ca$_v$3.2 has been found in various pain conditions, it will be of interest to address the analgesic efficacy of AAV-Ca$_v$3.2iPA1 for PSN T-type/Ca$_v$3.2 inhibition in additional models of other pain etiologies.

Nociceptor hyperexcitability induced by peripheral nerve injury is an established peripheral mechanism of neuropathic pain. Injury-induced ectopic hyperactivity of PSNs causes hypersensitization in multiple sites of the peripheral sensory nervous system, including augmented pain perception in the peripheral terminals, enhanced nociceptive signal transduction in PSN soma, and increased neurotransmission in the spinal dorsal horn. Our studies did not investigate differential actions by block of T-type/Ca$_v$3.2 along the pathway of nociceptors, nor did the results rule out the possibility that block of T-type/Ca$_v$3.2 reduces pain by inhibiting afferent hyperexcitable input, thus indirectly modulating CNS antinociceptive control circuits. The potential signaling pathways that the iPAs affected could be many, since Ca$_v$3.2 intracellular segments serve as essential interfaces for many regulatory signaling molecules, including deubiquitinating enzyme (USP5), Calcium/calmodulin-dependent protein kinase II (CaMKII), cyclin-dependent kinase 5 (Cdk5), G-proteins, calcineurin, calmodulin, syntaxin/SNAP25, and Stac1, and form protein complexes with members of the K$^+$ channel family, such as K$_v$4, K$_{Ca3.1}$, and K$_{Ca1.1}$ (BK), and K$^+$/Na$^+$ hyperpolarization-activated cyclic nucleotide-gated channel 1 (HCN1), as well as lipids. Alterations of these molecules and ion channels following nerve injury are essential for the ectopic PSN hyperactivity and pain.

Our data describe a strategy that addresses a significant hurdle in Ca$_v$3.2 peptide inhibitor discovered by targeting Ca$_v$3.2 IDRs. Ca$_v$3.2iPA1 is a promising analgesic lead that, combined with AAV-targeted gene delivery in anatomically segmental sensory ganglia, has the potential for future clinical development as novel therapeutics in the treatment of pain. And IDR approach is applicable to discover iPAs to many other pronociceptive ion channels for AAV-mediated peripheral analgesia.

Materials and Methods

Animals

Adult male Sprague Dawley (SD) rats weighing 100-125 g body weight (Charles River Laboratories, Wilmington, MA) were used. All animal experiments were performed with the approval of the Medical College of Wisconsin Institutional Animal Care and Use Committee (Permit number: 3690-03) in accordance with the National Institutes of Health Guidelines for the Care and Use of Laboratory Animals. Animals were housed individually in a room maintained at constant temperature (22±0.5° C.) and relative humidity (60±15%) with an alternating 12 h light-dark cycle. Animals were access to water and food ad libitum throughout the experiment, and all efforts were made to minimize suffering. For tissue harvest euthanasia, animals were deeply anesthetized by isoflurane followed by decapitation with a well-maintained guillotine. The estimated numbers of animals needed were derived from our previous experience with similar experiments and the number of experiments needed to achieve statistically significant deviation (20% difference at $p<0.05$) based on a power analysis.

In Computational (Silico) Designs

Rat $Ca_v3.2$ full amino acid sequence was retrieved from the UniProt KB knowledge database (UniProt Knowledgebase release 2018_11). $Ca_v3.2$ protein TM domains and intracellular termini and loops were predicted by Phobius. To identify specific IDRs, we analyzed the full-length rat $Ca_v3.2$ sequence using DEPICTER. Potential phosphorylation sites in the $Ca_v3.2$ full aa sequence were identified using Disorder Enhanced Phosphorylation Predictor (DEPP) and high-throughput papers (HTP) that phosphorylation sites are assigned by proteomic discovery mass spectrometry (PhosphoSitePlus v6.5.8). Potentially functional peptides (iPAs) within the IDRs were further analyzed using "Motifs", "Eukaryotic Linear Motif" (ELM), and SLIM-Prints which predict short linear motifs (SLiMs) based on strongly conserved SLIMs within IDRs followed by filtering based on the prediction scores. Peptide structure determination was analyzed by I-TASSER.

Molecular Cloning and AAV Constructs

To construct the AAV vector coding a chimeric GFP-$Ca_v3.2$iPA expression cassettes, the DNA fragments encoding the $Ca_v3.2$iPA peptides were synthesized and subcloned into BsrG I/Sal I sites (Genscript, Piscataway, NJ) of a single-strand AAV expressing plasmid pAAV-CBA-GFP. This generated pAAV-CBA-GFP-$Ca_v3.2$iPAs that codes the GFP-$Ca_v3.2$iPAs fusion protein downstream a chimeric intron for enhancing transcription driven by the CBA promoter and a mRNA stabilizing Woodchuck Posttranscriptional Regulatory Element (WPRE) sequence was inserted downstream of stop code of GFP-$Ca_v3.2$iPAs and upstream of human growth hormone poly A signals. Plasmids were used in transfection experiments and in AAV vector generation. Transfection on cultured cells was performed by a standard polyethylenimine (PEI, MW 40,000, Polysciences, Inc) transfection protocol. To package AAV2/6-EGFP-$Ca_v3.2$iPAs and AAV2/6-EGFP-NP as a control (subsequently referred to as AAV6-$Ca_v3.2$iPAs and AAV6-GFPNP, respectively) for in vivo injection, AAV vectors were produced and purified in our laboratory by previously described methods. This included AAV particle purification by optiprep ultracentrifugation and concentration using Centricon Plus-20 (Regenerated Cellulose 100,000 MWCO, Millipore, Billerica, MA). AAV titer was determined by PicoGreen (life technologies, Carlsbad, CA) assay, and final aliquots were kept in 1× phosphate buffered saline (PBS) containing 5% sorbitol (Sigma-Aldrich, St. Louis, MO) and stored at $-80°$ C. The titers (GC/ml) of AAV6-$Ca_v3.2$iPA1, 2, 3 and AAV6-GFPNP vectors were $2.45\times10^{13}$, $3.05\times10^{13}$, $2.64\times10^{13}$, and $2.26\times10^{13}$, respectively. The same lots of viral preparations were used for all in vivo experiments.

Cell Culture

HEK293 cell lines stably expressing human wide-type $Ca_v3.2$ (HEK3.2), $Ca_v3.1$ (HEK3.1), $Ca_v3.3$ (HEK3.3) (Kerafast. Boston, MA), $Ca_v2.2$ (HEK2.2, provided by Dr. Missler at Georg-August University, Germany), and neuronal NG108-15 (ATCC, Manassas, VA) were cultivated in Dulbecco's modified Eagle's medium supplemented with glutamax and 10% fetal bovine serum (Life technologies) and antibiotics using standard techniques.

Dissociated DRG neuron culture for electrophysiology was performed, as described previously. In brief, the DRG (L4 and L5) were rapidly harvested from the isoflurane-anesthetized animals and were incubated in 0.01% blendzyme 2 (Roche Diagnostics, Madison, WI) for 30 min followed by incubation in 0.25% trypsin and 0.125% DNase for 30 min, both dissolved in DMEM/F12 with glutaMAX (ThermoFisher). After exposure to 0.1% trypsin inhibitor and centrifugation, the pellet was gently triturated in culture medium containing Neural basal media A (ThermoFisher) plus 0.5 μm glutamine. Dissociated cells were plated onto 5% laminin-coated glass coverslips (ThermoFisher) and maintained at 37° C. in humidified 95% air and 5% $CO_2$ for 2 h, and were studied no later than 6 h after harvest in electrophysiological experiments.

Electrophysiological Recordings

Electrophysiological recordings were performed, as described previously with minor modification, in a blind manner where the electrophysiologist was not aware of the treatment. Patch pipettes, ranging from 2-4MΩ resistance, were formed from borosilicate glass (King Precision Glass Co., Claremont, CA) and fire polished. Recordings were made with an Axopatch 700B amplifier (Molecular Devices, Downingtown, PA). Signals were filtered at 2 kHz and sampled at 10 kHz with a Digidata 1440A digitizer and pClamp10 software (Molecular Devices). Series resistance (5-10MΩ) was monitored before and after the recordings, and data were discarded if the resistance changed by 20%. After achieving the whole cell recording, capacitance and series resistance were compensated accordingly. All experiments were performed at room temperature (22° C. to 25° C.).

T-Type Calcium Channel Current (Ice) on Cultivated Cell Lines

Modified Tyrode's solution consists of the following (in mM): 140 NaCl, 4 KCl, 2 $CaCl_2$), 2 $MgCl_2$, 10 D-glucose, 10 HEPES at pH of 7.4 with NaOH and an osmolarity of 300 mOsm. Voltage-induced currents flowing through $Ca^{2+}$ channels were recorded using an extracellular solution containing (in mM): 2 $BaCl_2$ (or $CaCl_2$)), 4-aminopyridine 1, 10 HEPES, 140 tetraethylammonium chloride (TEACl), pH of 7.4, with an osmolarity of 300 mOsm. It: recorded were elicited by 400 ms depolarizing steps ranging between −90 mV and +60 mV in 10 mV increments with 5-s intervals between steps from a holding potential of −100 mV. Measured inward current was normalized by membrane capacitance, which results in a T-channel $I_{Ca}$ density corrected for cell size (pA/pF). To determine the current-voltage (I-V) relationship of voltage-dependent activation, the peak $I_{Ca}$ densities during each voltage command step were fitted to a smooth curve with a Boltzmann equation: $I=G_{max}(V-E_{rev})/[(1+\exp[(V-V_{50})/k))]$, which provided the maximum conductance ($G_{max}$). Normalized activation curves were fitted with a Boltzmann equation $G/G_{max}=1/(1+\exp(V_{50}-Vm)/k)$, where G was calculated as follows: $G=I/(Vm-Erev)$. The steady-state inactivation curves were fitted with $I/Imax=1/(1+\exp-(V_{1/2}-Vm)/k)$. In all of the equations, $V_{1/2}$ denotes the half-activation and half inactivation potentials, Vm is the membrane potential, Erev is the inversion potential, k is the slope factor, G is the conductance, and I is the current at a given Vm; $G_{max}$ and $I_{max}$ are the maximum conductance and current, respectively.

Whole-Cell Voltage-Clamp Recording on Dissociated DRG Neurons

To record voltage-activated $I_{Ca}$, the internal pipette solution contained (in mM): 110 Cs-methylsulfate, 10 TEA-Cl, 1 $CaCl_2$, 1 $MgCl2$, 10 EGTA, 10 HEPES, 4 Mg-ATP, 0.3 $Li_2$-GTP, at pH of 7.2 with CsOH and osmolarity of 296 to 300 mOsm. Small- to medium-size PSNs (<40 μm soma diameter) were chosen to record T-type low-voltage activated (LVA) $I_{Ca}$ because these are likely nociceptors and have T-type currents under normal conditions. To selectively record T-LVA $I_{Ca}$ from DRG dissociated cultures, neurons were preincubated in a Tyrode's solution with 0.2 μM @-conotoxin GVIA, 0.2 μM nisoldipine and 0.2 μM @-conotoxin MVIIC for at least 30 min. ω-conotoxin GVIA irreversibly blocks N-type $I_{Ca}$, and ω-conotoxin MVIIC irreversibly blocks P-/Q-type $I_{Ca}$. The concentrations used were saturating in preliminary experiments. Any residual high-voltage activated (HVA) $I_{Ca}$ following incubation of HVA calcium channel blockers was eliminated by using fluoride in the internal pipette solution. The fluoride (F)-based internal solution, which was used in all experiments examining LVA $I_{Ca}$, contained (in mM): 135 tetra-methyl ammonium hydroxide (TMA-OH), 10 EGTA, 40 HEPES, and 2 $MgCl_2$, adjusted to pH 7.2 with hydrofluoric acid (HF). A selective and reversible T-type $Ca^{2+}$ channel blocker, TTA-P2 (3, 5-dichloro-N-[1-(2,2-dimethyl-tetrahydropyran-4-ylmethyl)-4-fluoro-piperidin-4-ylmethyl]-benzamide, Alomone Labs, Jerusalem, Israel), was used to confirm the T-type $I_{Ca}$. Leak currents were digitally subtracted using a P/4 leak subtraction protocol. The peak T-current was measured after subtracted from the current at the end of the depolarizing test potential to avoid contamination with residual HVA currents. Voltage protocols consisted of 100-ms depolarizing steps from a holding potential of −60 mV for HVA, or 400-ms depolarizing steps from a holding potential of −90 mV for LVA to +60 mV, in 10-mV increments with 5-s intervals between steps.

Whole-Cell Current-Clamp Recording in Dissociated DRG Neurons

Whole-cell current-clamp recording of dissociated DRG neurons was performed as described previously, to determine the effects of AAV-mediated $Ca_v3.2iPA1$ on neuronal excitability. Dissociated small- and medium-sized DRG neurons (<40 μm in diameter) from sham-operated animals and rats with TNI only, and dissociated DRG neurons with clear GFP expression from TNI rats injected with AAV6-GFPNP or AAV6-$Ca_v3.2iPA1$ at 5-week after TNI and vector injection were used for recording (n=5 rats per group). Dissociated cells were studied no later than 6 h after harvest. For whole-cell current-clamp, patch electrodes had a resistance of 0.7-1.5 MΩ when filled with the pipette solution, which contained the following (in mM): 140 K-gluconate, 5 KCl, 2 $MgCl_2$. 0.2 EGTA, 10 HEPES, 4 Mg-ATP, and 0.3 $Na^{2+}$-GTP, 10 Na2-phosphocreatine pH 7.2 with KOH and osmolarity of 296 to 300 mOsm. The extracellular solution contained the following (in mM): 140 NaCl, 4 KCl, 2 $CaCl_2$), 2 $MgCl_2$, 10 D-glucose, 10 HEPES at pH of 7.4 with NaOH and an osmolarity of 300 mOsm. Whole-cell configuration was obtained in voltage-clamp mode before proceeding to the current-clamp recording mode. The membrane input resistance was calculated by dividing the end amplitude of steady-state hyperpolarizing voltage deflection by the injected current. Action potentials (APs) were generated by injection of a series of current pulses (100 to 1000 pA in steps of 100 pA, 250 ms). The baseline potential had been recorded for 20 ms before the stimulus pulses were injected into the neurons. We defined the resting membrane potential (RMP) as the mean value of the 20 ms pre-stimulus potential in the first trial and the AP rheobase as the minimum current required to evoke the first AP. Given the knowledge that nerve injury induces high RMP and low rheobase in DRG neurons, the neurons with stable resting membrane potentials (RMP) more negative than-40 mV and overshooting APs (>80 mV RMP to peak) were used for additional data collection. AP frequency was determined by quantifying the number of APs elicited in response to depolarizing current injections (250 ms).

Measurement of cytoplasmic $Ca^{2+}$ concentration

Measurement of cytoplasmic $Ca^{2+}$ concentration ($[Ca^{2+}]_c$) was performed following our previously published protocols. In brief, neurons plated on coverslips were exposed to Fura-2-AM (5 μM) at room temperature in a solution that contained 2% bovine albumin to aid dispersion of the fluorophore. After 30 min, they were washed 3 times with regular Tyrode's solution, given 30 minutes for de-esterification, and then mounted in the recording chamber. Neurons were first examined under bright field illumination, and those showing signs of lysis, crenulation or superimposed glial cells were excluded. For $[Ca^{2+}]_c$ recording, the fluorophore was excited alternately with 340 nm and 380 nm wavelength illumination (150 W Xenon, Lambda DG-4, Sutter, Novato, CA), and images were acquired at 510 nm using a cooled 12-bit digital camera (Coolsnapfx, Photometrics, Tucson, AZ) and inverted microscope (Diaphot 200, Nikon Instruments, Melville, NY) through a 20X objective. Recordings from each neuron were obtained as separate regions (MetaFluor, Molecular Devices) at a rate of 3 Hz. After background subtraction, the fluorescence ratio R for individual neurons was determined as the intensity of emission during 340 nm excitation (1340) divided by 1380, on a pixel-by-pixel basis. Transient changes in $[Ca^{2+}]_c$ were generated by depolarization produced by microperfusion application of $K^+$ (50 mM) for 0.3 s which is T-channel specific.

Microinjection of AAV Vectors into DRG

AAV vector solution was microinjected into right L4 and L5 DRG using previously described techniques. Briefly, the surgically exposed intervertebral foramen was minimally enlarged by removal of laminar bone. Injection was performed through a micropipette that was advanced ~100 μm into the ganglion. Rats received L4 and L5 DRG injections of either AAV6-CBD3A6K or AAV6-EGFP (one vector per rat), consisting of 2 μl with adjusted titers containing a total of $2.0 \times 10^{10}$ genome viral particles. Injection was performed over a 5-min period using a microprocessor-controlled injector (Nanoliter 2000, World Precision Instruments, Sarasota, FL, USA). Removal of the pipette was delayed for an additional 5 min to minimize the extrusion of the injectate. Following the injection and closure of overlying muscle and skin, the animals were returned to their housing where they remained as the designed experiments required.

Animal Pain Model and Behavior Testing

Tibial nerve injury. To model clinical traumatic painful peripheral neuropathy, we performed a TNI, an established model of peripheral nerve injury. Animals were anesthetized using isoflurane at 4% for induction and 2% for maintenance. Under anesthesia, the right sciatic nerve was exposed under aseptic surgical conditions by blunt dissection of the femoral biceps muscle. The sciatic nerve and its three branches (sural, common peroneal, and tibial nerves) were isolated. The tibial nerve was then tightly ligated and transected distal to the ligation. The overlying muscle and skin were then sutured following surgery. Sham-operated rats were subjected to all preceding procedures without nerve ligation and transection.

Behavior testing. Behavioral tests were conducted between 9:00 AM and 12:00 AM. Experimenters were blinded to the treatment. Animals were habituated in individual test compartments for at least one hour before each testing. Behavioral tests, including mechanical withdrawal threshold testing (von Frey), noxious punctate mechanical stimulation (pin test), and thermal stimulation, were carried out as previously described.

Immunohistochemistry (IHC)

The previously described protocol was adopted. In brief, the formalin-fixed, paraffin-embedded (FFPE) tissue sections were deparaffinized, hydrated, and treated by heat-induced antigen epitope retrieval in 10 mM citrate buffer, pH 6.0. Non-specific binding was reduced by incubating the sections for 30 min with a solution of 5% BSA in PBS plus 0.05% Tween20 (PBST) solution. Samples were first immunolabeled with the selected primary antibodies (GFP 1:100, $Ca_v3.2$ 1:100, CGRP 1:100, and IB4 1.0 μg/ml; all described previously) in a humid atmosphere overnight at 4° C. All antibodies were diluted in PBST, containing 0.05% Triton X-100 and 5% bovine serum albumin (BSA). Normal immunoglobulin G (IgG from the same species as the first antibody was replaced for the first antibody as the negative controls. The appropriate fluorophore-conjugated (Alexa 488 or Alexa 594, 1:2000) secondary antibodies (Jackson ImmunoResearch, West Grove, PA) were used to reveal immune complexes. Afterward, the sections were rinsed for 10 min in PBS and either processed for a colabeling of primary and secondary antibodies or coverslipped under Shur/Mount mounting medium (ThermoFisher). To avoid false-positive results attributable to cross-binding in double-label combinations, each primary antibody raised in a different species was used. To stain nuclei, 1.0 μg/ml Hoechst33342 (Hoechst, ThermoFisher) was added to the secondary antibody mixture. The immunostaining was examined, and images were captured using a Nikon TE2000-S fluorescence microscope (El Segundo, CA) with filters suitable for selectively detecting the green and red fluorescence using a QuantiFire digital camera (Optronics, Ontario, NY). For double-label colocalization, images from the same specimen but showing different antigen signals were overlaid by digitally merging the captured images.

Immunoblot

Cell lysates from cultivated cells lines and DRG tissue lysates from pooled L4/L5 DRG were prepared using 1× RIPA ice-cold buffer (20 mm Tris-HCl pH 7.4, 150 mm NaCl, 1% Nonidet P-40, 1% sodium deoxycholate, 0.1% SDS, with 0.1% Triton X100 and protease inhibitor cocktail) and rotated at 4° C. for 1 h before the supernatant was extracted by centrifugation at 12,000 g at 4° C. for 5 min. To examine the subcellular localization of $Ca_v3.2$, NG108-15 cells and DRG tissue were homogenized and then fractionated to obtain plasma membrane, cytosolic, and nuclear using the ProteoExtract Subcellular Proteome Extraction Kit (Millipore, Billerica, MA), according to the manufacturer's instructions. This kit contains extraction buffers with ultra-pure chemicals to ensure high reproducibility, protease inhibitor cocktail to prevent protein degradation, and benzonase nuclease to remove contaminating nucleic acids. Protein concentration was determined using Pierce BCA kit (ThermoFisher). Equivalent protein samples were size separated using 10% or 4-20% SDS-PAGE gels (Bio-Rad), transferred to Immun-Blot PVDF membranes (Bio-Rad), and blocked for 1 hr in 5% skim milk. In some experiments, the transferred PVDF membranes were cut into two halves along protein size around 70 KDa and were subsequently incubated overnight at 4° C. with appropriate antibodies. Immunoreactive proteins were detected by Pierce enhanced chemiluminescence (ThermoFisher) on a ChemiDoc Imaging system (Bio-Rad) after incubation for 1 hr with HRP-conjugated second antibodies (1:5000, Bio-Rad).

Statistical Analyses

Statistical analysis was performed with GraphPad PRISM 9 (GraphPad Software, San Diego, CA). Behavioral changes compared to pre-treatment baseline and between groups for von Frey measurements were generated using repeated measures two-way ANOVA and post-hoc analysis with Bonferroni test. Pin and cold test results in discrete numerical data without normal distribution so conservative non-parametric analysis was performed by Friedman's test for analysis of variance and Dunn's test for post hoc analysis. Results are reported as mean and standard deviation of mean (SEM). For electrophysiological data, the effect of nerve injury by TNI was determined by comparison to findings in naïve animals with Mann-Whitney nonparametric t-test, and the effect of the two vectors was compared to non-injected TNI animals using nonparametric Kruskal-Wallis ANOVA with Dunn's test for paired comparisons. $P<0.05$ were considered statistically significant.

We claim:
1. A fusion protein comprising:
   (a) at least one inhibitory polypeptide, the inhibitory polypeptide selected from the group consisting of SEQ ID NOs: 1, 2, 4, and 5; and
   (b) a polypeptide scaffold or tag;
   wherein (a) is linked by a linker sequence to (b),
   wherein the fusion protein does not include a $Ca_v3.2$ transmembrane domain, and
   wherein the fusion protein binds specifically to a human $Ca_v3.2$ protein and inhibits a human $Ca_v3.2$ protein function.
2. The fusion protein of claim 1, further comprising two or more inhibitory polypeptides selected from the group consisting of SEQ ID NOs: 1-5 linked by an additional linker sequence, wherein at least one of the two or more inhibitory polypeptides is selected from the group consisting of SEQ ID NOs: 1, 2, 4, and 5.
3. A pharmaceutical composition comprising the fusion protein of claim 1, and a pharmaceutically acceptable carrier.
4. A nucleic acid construct comprising a polynucleotide sequence encoding a fusion protein and a heterologous promoter sequence, the fusion protein comprising:
   (a) at least one inhibitory polypeptide, the inhibitory polypeptide selected from the group consisting of SEQ ID NOs: 1, 2, 4, and 5; and
   (b) a polypeptide scaffold or tag;
   wherein (a) is linked by a linker sequence to (b),
   wherein the fusion protein does not include a $Ca_v3.2$ transmembrane domain, and wherein the fusion protein binds specifically to a human $Ca_v3.2$ protein and inhibits a human $Ca_v3.2$ protein function.
5. The nucleic acid construct of claim 4, wherein the construct is a vector.
6. The nucleic acid construct of claim 5, wherein the vector is a viral vector.
7. The nucleic acid construct of claim 6, wherein the viral vector is an adeno-associated virus (AAV) vector.
8. A pharmaceutical composition comprising the nucleic acid construct according to claim 4 and a pharmaceutically acceptable carrier.
9. An adeno-associated virus (AAV) comprising a heterologous nucleic acid sequence, encoding a fusion protein, operably linked to a regulatory sequence(s) which directs expression of the fusion protein in a host cell, the fusion protein comprising:
   (a) at least one inhibitory polypeptide, the inhibitory polypeptide selected from the group consisting of SEQ ID NOs: 1, 2, 4, and 5; and
   (b) a polypeptide scaffold or tag;
   wherein (a) is linked by a linker sequence to (b),
   wherein the fusion protein does not include a $Ca_v3.2$ transmembrane domain, and wherein the fusion protein binds specifically to a human $Ca_v3.2$ protein and inhibits a human $Ca_v3.2$ protein function.
10. The adeno-associated virus (AAV) of claim 9, wherein the AAV is AAV type 1, AAV type 2, AAV type 3, AAV type 4, AAV type 5, AAV type 6, AAV type 7, AAV type 8, AAV type 9, AAV type 10, or AAV type 11.
11. A pharmaceutical composition comprising the adeno-associated virus (AAV) of claim 9 and a pharmaceutically acceptable carrier.
12. A fusion protein comprising:
   (a) a first region, the first region comprising one or more $Ca_v3.2$ sequences, the $Ca_v3.2$ sequences selected from the group consisting of: SEQ ID NOs: 1, 2, 4, and 5; and
   (b) a second region, the second region consisting of a non-$Ca_v3.2$ protein scaffold;
   wherein the fusion protein binds specifically to a human $Ca_v3.2$ protein and inhibits a human $Ca_v3.2$ protein function, and wherein the fusion protein does not include a $Ca_v3.2$ transmembrane domain.
13. A method of treating pain in a subject in need thereof, the method comprising administering a therapeutically effective amount of:
   (a) a fusion protein according to claim 1
   wherein pain in the subject is treated.
14. The method of claim 13, wherein administering comprises targeted delivery to a dorsal root ganglion (DRG) of the subject, whereby the fusion protein inhibits $Ca_v3.2$ T-type calcium channel activity in the dorsal root ganglion (DRG).
15. The method of claim 13, wherein the administering comprises injecting a therapeutically effective amount of AAV particles encoding the fusion protein into a dorsal root ganglion of the subject, whereby the fusion protein is expressed and inhibits $Ca_v3.2$ T-type calcium channel activity.
16. The method of claim 13, wherein the administering results in reducing nociceptive dorsal root ganglion (DRG) neuron excitation.
17. The method of claim 13, wherein said pain is chronic pain or neuropathic pain.
18. A method of inhibiting a $Ca_v3.2$ T-type calcium channel activity in the dorsal root ganglion (DRG) in a subject in need thereof, the method comprising administering to the dorsal root ganglion a therapeutically effective amount of:
   (a) a fusion protein according to claim 1 wherein $Ca_v3.2$ T-type calcium channel activity is inhibited.
19. The method of claim 18, wherein the administering is via local administration.
20. The method of claim 18, wherein the administering comprises injecting a therapeutically effective amount of AAV particles encoding the fusion protein into a dorsal root ganglion of the subject, whereby the fusion protein is expressed and inhibits $Ca_v3.2$ T-type calcium channel activity.
21. The method of claim 18, wherein the administering results in reducing nociceptive dorsal root ganglion.

* * * * *